(12) United States Patent
Atencio et al.

(10) Patent No.: US 7,001,770 B1
(45) Date of Patent: Feb. 21, 2006

(54) CALPAIN INHIBITORS AND THEIR APPLICATIONS

(75) Inventors: Isabella A. Atencio, San Diego, CA (US); Drake M. LaFace, San Diego, CA (US); Muralidhara Ramachandra, San Diego, CA (US); Paul W. Shabram, Olivenhain, CA (US)

(73) Assignee: Canji, Inc., San Diego, CA (US)

( * ) Notice: Subject to any disclaimer, the term of this patent is extended or adjusted under 35 U.S.C. 154(b) by 0 days.

(21) Appl. No.: 09/416,735

(22) Filed: Oct. 13, 1999

Related U.S. Application Data

(60) Provisional application No. 60/104,321, filed on Oct. 15, 1998.

(51) Int. Cl.
  *C12N 15/00* (2006.01)
  *C12N 15/63* (2006.01)
  *C12N 15/85* (2006.01)
  *C12N 15/86* (2006.01)

(52) U.S. Cl. ............... 435/455; 435/440; 435/456

(58) Field of Classification Search .......... 514/44; 424/93.1, 93.2, 93.21; 435/320.1, 455, 440, 435/456
See application file for complete search history.

(56) References Cited

U.S. PATENT DOCUMENTS 6,015,787 A * 1/2000 Potter et al. ............... 514/12

OTHER PUBLICATIONS

Atencio, I. A. et al., "Calpain Inhibitor 1 Activates p53-dependent Apoptosis in Tumor Cell Lines" Cell Growth & Differentiation, vol. 11, pp. 247-253, May 2000.*
Friedmann, T. "Overcoming the Obstacles to Gene Therapy" Scientific American, pp. 96-101, Jun. 1997.*
Gonen, H. et al., "On the involvement of calpains in the degradation of the tumor suppressor protein p53" FEBS Letters, vol. 406, pp. 17-22, 1997.*
Hodgson, C. P. "Advances in vector systems for gene therapy" Exp. Opin. Ther. Patents, vol. 5, pp. 459-468, May 1995.*
Orkin S. H. and Motulsky A. G. ,"Report and Recommendations of the Panel to assess the NIH investment in research on Gene therapy", Dec. 7, 1995.*
Verma, I. M. and Somia N. ,"Gene therapy- promises, problems and prospects" Nature, vol. 389, pp. 239-242, Sep. 18, 1997.*
Claudio et al. (1996) Molecular mechanisms of TNFalpha cytotoxicity: Activation of NF-kappaB and nuclear translocation. Experimental Cell Research 224(1): 63-71.*

* cited by examiner

*Primary Examiner*—Anne-Marie Falk
(74) *Attorney, Agent, or Firm*—Townsend and Townsend and Crew LLP

(57) ABSTRACT

The present invention provides a method to enhance apoptosis in a cell by the administration of p53 in combination with a calpain inhibitor. The present invention provides a method of increasing the infectivity of a cell to a viral vector by treatment of the cell with a calpain inhibitor. the present invention further provides a method of enhancing transcription of a therapeutic transgene from the CMV promoter. The present invention also provides a method of suppress the in vivo CTL response to viral vectors by the use of calpain inhibitors. The present invention further provides a pharmaceutical formulations of p53 and a calpain inhibitor in a pharmaceutically acceptable carrier. The present invention provides a method of ablating neoplastic cells in a mammalian organism in vivo by the co-administration of a calpain inhibitor and p53. The present invention also provides a method of ablating neoplastic cells in a population of normal cells contaminated by said neoplastic cells ex vivo by the administration of a recombinant adenovirus in combination with a calpain inhibitor to said population.

19 Claims, 15 Drawing Sheets

SEQUENCE LISTING

<160> NUMBER OF SEQ ID NOS: 7

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence:
      immunoglobulin light chain kappa enhancer region nuclear factor
      kappa B (NFkB) specific DNA binding sequence

<400> SEQUENCE: 1
ggggactttc c                                                          11

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide Primer "A" (5' Taqman p53)

```
<400> SEQUENCE: 2
aacggtactc cgccacc                                                         17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide Primer "B" (3' Taqman p53)

<400> SEQUENCE: 3
cgtgtcaccg tcgtgga                                                         17

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:p53 Taqman
      Probe
<220> FEATURE:
<221> NAME/KEY: modified_base
<222> LOCATION: (1)
<223> OTHER INFORMATION: n = c modified by FAM
<220> FEATURE:
<221> NAME/KEY: modified_base
<222> LOCATION: (26)
<223> OTHER INFORMATION: n = c modified by TAMRA

<400> SEQUENCE: 4
nagctgctcg agaggttttc cgatcn                                               26

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:B-Actin
      Primer "A" (5' Taqman B-Actin)

<400> SEQUENCE: 5
tcacccacac tgtgcccatc tacga                                                25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:B-Actin
      Primer "B" (3' Taqman B-Actin)

<400> SEQUENCE: 6
cagcggaacc gctcattgcc aatgg                                                25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:B-Actin
      Taqman Probe
<220> FEATURE:
<221> NAME/KEY: modified_base
<222> LOCATION: (1)
<223> OTHER INFORMATION: n = c modified by FAM
<220> FEATURE:
<221> NAME/KEY: modified_base
```

```
<222> LOCATION: (25)
<223> OTHER INFORMATION: n = c modified by TAMRA

<400> SEQUENCE: 7 ntgcccccccc catgccatcc tgcgn                                              25
```

CALPAIN INHIBITORS AND THEIR APPLICATIONS

This application claims the benefit of U.S. Provisional Application Ser. No. 60/104,321 filed Oct. 15, 1998 pursuant to 35 U.S.C. 119.

BACKGROUND OF THE INVENTION

Programmed cell death is a natural process by which an organism eliminates particular cells in a regulated process. Programmed cell death pathways are initiated by a variety of stimuli, some internal to the cell (e.g. DNA damage) while others are activated as a result of external factors (e.g. fas ligand). To date, a single mediator of apoptosis has not been elucidated. Rather, a variety of apoptotic mechanisms are in a potential state for response at all times. The fact that many molecules are identified as possessing both pro- and anti-apoptotic activity (e.g. caspases, NF-kB, AP1, and p53), there appears to be a fine balance of factors which permit survival or terminate the cell.

While no single mediator of apoptosis has been identified, mutations in p53 are recognized as the most common genetic alterations associated with human cancer, diseases characterized by abberent regulation of cell cycle control and apoptosis. Although p53 was first characterized as a dominant cooperating oncogene, it was later determined that the form of p53 under investigation at that time was a mutant, inactive and long-lived form of the wild-type protein. This mutant protein displaced the short-lived wild-type native form from its enzymatic substrate binding sites and was mistakenly deemed to act dominantly. p53 is now thought of as a tumor suppressor gene.

The sequence specific DNA binding properties of p53 regulate the transcription of a continually expanding number of genes involved in regulation of the cell cycle and apoptosis. p53 has been implicated in the transcriptional downregulation of the bcl2 gene and upregulation of the bax gene, precipitating a cascade of events leading to apoptosis. The complete mechanism of action of p53 is not fully elucidated. Though it is known that p53 binds to many important cellular proteins and is involved in the control of gene expression, cell cycle regulation and apoptosis, it is observed that some tumors produce wildtype p53, yet do not undergo apoptosis. The intracellular cytosolic concentration of p53 appears to be maintained by a balance of continual synthesis and degradation. p53 exists as an inactive cytosolic monomeric protein with a very short half-life. Increasing data support the view that, in normal cells, stability of p53 is controlled through mdm-2 -binding and ubiquination, through an, as yet, incompletely understood mechanism. Binding of p53 to mdm-2 has been shown to lead to ubiquitination of p53 protein. Following ubiquitination, the p53 is believed to be degraded through a common proteasome mediated degradative pathway. p53 exerts its function as a tetramer of phosphorylated p53 subunits. The phosphorylation step leading to activation of p53 function is mediated by DNA-dependent protein kinase ("DNA-PK"). DNA-PK appears to be activated in response to DNA damage. Woo, et al. (1998) Nature 394:700–704; Lane, D. (1998) Nature 394:616–617.

While not the sole mechanism of apoptosis, the p53 apoptotic pathway is clearly an important pathway employed by the organism to eliminate aberrant cell types. p53 has been demonstrated to play a role in many biochemical pathways related to human carcinogenesis. In approximately 50% of human cancers, the p53 gene is inactivated through mutational, viral, or other cellular components. Somatic mutations in the DNA binding domain of p53 are found in the majority of human tumors bearing p53 alterations. It has been demonstrated that restoration of p53 function in p53 deficient tumor cells will induce apoptosis of tumor cells. Currently, replication defective recombinant adenovirus vectors expressing wildtype p53 (rAd-p53) are being used in human clinical trials (Nielsen and Maneval, 1998). To date, more than 137 human patients have been treated with rAd-p53. Initial results of these trials demonstrate acceptable safety profies and therapeutic effect of such vectors in vivo.

Calpain, a calcium dependent cysteine protease, has recently been implicated to play a role in apoptosis. Calpain has two primary isoforms (m-calpain and $\mu$-calpain) distinguished by the calcium concentration required for their activation in vitro. Calpain consists of a heavy and light chain. The heavy chain consists of a cysteine proteinase domain. The light chain is a calcium binding domain and possesses four EF-hands characteristic of calcium binding proteins. The native form of calpain is inactive except at relatively high Ca+2 concentrations. In vitro experiments indicate that $\mu$-calpain (also known as calpain I) requires $\mu$M calcium levels for activation. In contrast, m-calpain (also known as calpain II) requires a much higher (mM) calcium concentration for activation. Calpain is a cytosolic protease whose activity is modulated by the cytosolic inhibitor protein, calpastatin. Upon activation, calpain has been shown to translocate to the cell membrane where it is sequestered from its inhibitors (Lane et al., 1992; Molinari and Carafoli, 1997).

Additionally, calpain has been shown to possess in vitro proteolytic action against a broad range of substrates including components of receptor signaling pathways, interleukin receptors where the common cytokine receptor $\gamma$ chain is cleaved by calpains (Noguchi, et al. (1997) Proc Natl Acad Sci USA 94, 11534–9), cytoskeletal and focal adhesion proteins (Schoenwaelder, et al. (1997) J. Biol. Chem 272: 1694–702.), integrins (Du, et al. (1995) J Biol Chem 270, 26146–51; Inomata, et al. (1996) Arch Biochem Biophys 328, 129–34.; Palecek, et al. (1998) J. Cell Sci. 111, 929–40), and transcriptional factors such as c-fos and c-jun (Jariel-Encontre, I., Salvat, C., Steff, A. M., Pariat, M., Acquaviva, C., Furstoss, O., and Piechaczyk, M. (1997) Mol Biol Rep 24, 51–6.; Suzuki, K., Saido, T. C., and Hirai, S. (1992) Ann N Y Acad Sci 674, 218–27.), NF-kappa B (Claudio, et al. (1996) Exp Cell Res 224, 63–71.; Liu, et al. (1996) FEBS Lett 385, 109–13.), NF2 (Kimura, et al. (1998) Nature Medicine 4:915–922) and p53 (Gonen, et al. (1997) FEBS Lett 406, 17–22.; Kubbutat, M. H., and Vousden, K. H. (1997) Mol Cell Biol 17, 460–8.).

Although calpains demonstrate a broad range of substrates in vitro, its role in vivo remains unclear. As a consequence of their broad substrate specificity, the therapeutic applications suggested for calpain inhibitors include the prevention of neurodegradations and cellular damage caused by excessive activation of glutamate receptors in neuronal cells, retarding cataract formation, minimization of degeneration of neuronal tissues following injury, mycoardial infaction, angioplastic restenosis, prevention of cartilage damage and subsequent inflammation, muscular dystrophy and platelet aggregation associated with thrombosis. In vivo experiments in mice and rats have shown that prior infusion of calpain inhibitors prevents neuronal and hepatocyte cell death due to hypoxia, and increases survival after orthotopic liver transplants. In vitro, calpain inhibitors have been observed to attenuate apoptosis in primary rat hepatocytes in response to a variety of apoptotic stimuli. Additionally, calpain inhibitors have been shown to inhibit activation-induced programmed cell death of T-cells from HIV positive donors (Sarin et al., 1994). Calpain has been shown to cleave the precursor form of IL-1a into a 17 kD C-terminal fragment referred to as "mature" IL-1a and a 16 kD N-terminal fragment which migrates to the nucleus and induces apoptosis in vitro. In each of these instances, the primary application of the calpain inhibitor is to prevent cell death.

p53 gene therapy has focused on the use of recombinant viral, particularly adenoviral, vectors to result in the intracellular expression of p53. In such therapeutic regimens, a significant excess of the recombinant virus must be administered to the patient because not every viral particle administered will infect the target cell. This is due at least in part to the effects of diffusion, clearance and/or neutralization by the organism, and that not every interaction between the viral particle and a target cell results in infection and productive expression. However, the systemic administration of excess recombinant virus poses potential safety concerns to the individual undergoing treatment. Consequently, methods which can be employed to lower the total dose of the recombinant viral vector while maintaining a therapeutically effective dose are desired. The present invention provides a method of inducing apoptosis in p53 positive tumor cells by the administration of a calpain inhibitor alone or in combination with rAd-p53 or in combination with rAd-p53 and in tumors with mutated or null p53 status. The present invention also provides a decreased CTL response to the administration of recombinant adenoviral vectors by the concomitant administration of calpain inhibitors. The combined effect being increased p53 expression.

SUMMARY OF THE INVENTION

The present invention provides a method to enhance p53-mediated apoptosis in a cell by the administration of p53 in combination with a calpain inhibitor. The present invention further provides a method of inducing cell death in p53 positive tumor cells by the administration of a therapeutically effective dose of a calpain inhibitor. The present invention further provides a method of increasing the infectivity of a cell to a viral vector by treatment of the cell with a calpain inhibitor. The present invention further provides a method of enhancing transciption of a therapeutic transgene from the CMV promoter. The present invention further provides a method of suppressing the in vivo CTL response to viral vectors by the use of calpain inhibitors. The present invention further provides pharmaceutical formulations of p53 and a calpain inhibitor in a pharmaceutically acceptable carrier. The present invention further provides a method of ablating neoplastic cells in a mammalian organism in vivo by the co-administration of a calpain inhibitor and p53. The present invention further provides a method of ablating neoplastic cells in a population of normal cells contaminated by said neoplastic cells ex vivo by the administration of a recombinant adenovirus in combination with a calpain inhibitor.

DETAILED DESCRIPTION OF THE INVENTION

Figure 1:
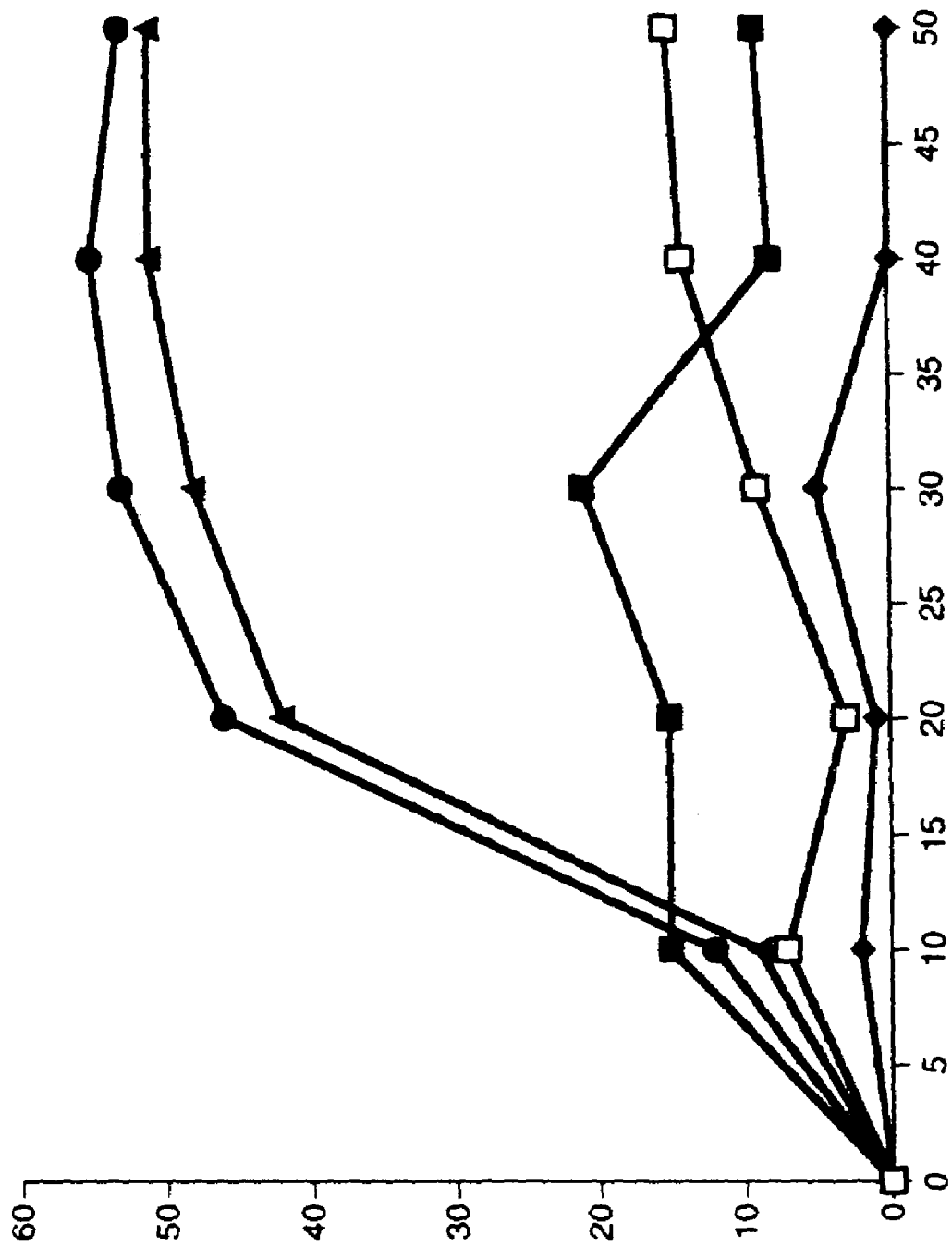
FIG. 1 is a graphical representation percentage of cells undergoing apoptosis (as determined by annexin V-FITC positive staining) in response to increasing concentrations of CI-1 in the SK-Hep1 (●) RKO(Δ), HLF (■), DLD1(□) and the HEP3B(♦) cell lines. The vertical axis represents the change in the percentage annexin V-FITC positive staining cells as determined by flow cytometry. The horizontal axis represents the $\mu$M concentration of CI-1.

A: Administration of Calpain Inhibitor in Combination with P53 Enhances Apoptosis The present invention provides a method to enhance apoptosis in a cell by the administration of p53 in combination with a calpain inhibitor.

The term "apoptosis" means a form of programmed cell death that is characterized by specific morphologic and biochemical properties. Morphologically, apoptosis is characterized by a series of structural changes in dying cells: blebbing of the plasma membrane, condensation of the cytoplasm and nucleus, and cellular fragmentation into membrane apoptotic bodies. Biochemically, apoptosis is characterized by the degradation of chromatin, initially into large fragments of 50–300 kilobases and subsequently into smaller fragments that are monomers and multimers of 200. The execution of apoptosis minimizes the leakage of cellular constituents from dying cells. This distinguishes apoptosis from necrosis, which usually results from trauma that causes injured cells to swell and lyse, releasing the cytoplasmic material that stimulates an inflammatory response.

The term "p53" refers to the product of the p53 tumor suppressor gene. The p53 protein is well known in the art. Nucleotide sequences encoding p53 may be isolated from libraries or synthesized using known techniques. As used herein, the term "p53" refers to the the wild-type p53 protein as well as mutations or truncations thereof, which display essentially the same function as the wild-type protein. It will be readily apparent to those of skill in the art that modifications and or deletions to the above referenced genes so as to encode functional subfragments of the wild type protein may be readily adapted for use in the practice of the present invention. For example, the reference to the p53 gene includes not only the wild type protein but also modified p53 proteins. Examples of such modified p53 proteins include modifications to p53 to increase nuclear retention, deletions such as the Δ13–19 amino acids to eliminate the calpain consensus cleavage site, modifications to the oligomerization domains (as described in Bracco, et al. PCT published application WO97/0492 or U.S. Pat. No. 5,573,925). The term p53 includes p53 molecules derived from human as well as other mammalian sources such as porcine p53, equine p53, bovine p53, canine p53, etc. It will be readily apparent to those of skill in the art that p53 may be secreted into the media or localized to particular intracellular locations by inclusion of a targeting moiety such as a signal peptide or nuclear localization signal (NLS). Also included in the definition of p53 are fusion proteins of the therapeutic transgene with the herpes. simplex virus type 1 (HSV-1) structural protein, VP22. See, e.g. Elliott, G. & O'Hare, P. Cell. 88:223–233:1997; Marshall, A. & Castellino, A. Research News Briefs. Nature Biotechnology. 15:205:1997; O'Hare, et al. PCT publication WO97/05265 published Feb.

13, 1997. A similar targeting moiety derived from the HIV Tat protein is also described in Vives, et al. (1997) J. Biol. Chem. 272:16010–16017.

The term "administration of p53" refers to p53 gene therapy as well as p53 protein therapy. The term "p53 gene therapy" refers to the introduction to a cell of a nucleotide sequence encoding p53 operably linked to expression control sequences so as to effect expression (transcription and translation) of the the p53 gene in the cell. The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleotide sequences being linked are typically contiguous. However, as enhancers generally function when seperated from the promoter by several kilobases and intronic sequences may be of variable lengths, some polynucleotide elements may be operably linked but not directly flanked and may even function in trans from a different allele or chromosome.

p53 gene therapy includes both in vivo and ex vivo gene therapy. Ex vivo gene therapy refers to the administration of an expression vector comprising a nucleotide sequence encoding p53 to a population cells obtained from a living organism with the expectation of those cells being reimplanted into the organism. Ex vivo gene therapy is described in Anderson, et al. U.S. Pat. No. 5,399,346 issued Mar. 21, 1995. Examples of ex vivo gene therapy include the purging of tumor cells from stem cell products. In vivo gene therapy refers to the administration of an expression vector comprising a nucleotide sequence encoding p53 to a living organism. Examples of in vivo gene therapy administration include intratumoral, regional (intraperitoneal) or subcutaneous (IM or IV) administration.

The term "expression vector" refers to viral an non-viral vectors comprising a p53 expression cassette. The term "expression cassette" is used herein to define a nucleotide sequence containing regulatory elements and a transgene coding sequence so as to result in the transcription and translation of a transgene in a transduced cell. The term "regulatory element" refers to promoters, enhancers, transcription terminators, polyadenylation sites, and the like. The expression cassette may also contain other sequences aiding expression and/or secretion of the therapeutic gene. The regulatory elements may be arranged so as to allow, enhance or facilitate expression of the transgene only in a particular cell type. For example, the expression cassette may be designed so that the transgene is under control of an inducible promoter, tissue specific or tumor specific promoter, or temporal promoter. The term "inducible promoter" refers to promoters which facilitate transcription of the therapeutic transgene preferable (or solely) under certain conditions and/or in response to external chemical or other stimuli. Examples of inducible promoters are known in the scientific literature (See, e.g. Yoshida and Hamada (1997) Biochem. Biophys. Res. Comm. 230:426–430; lida, et al. (1996) J. Virol. 70(9):6054–6059; Hwang, et al. (1997) J. Virol 71(9):7128–7131; Lee, et al. (1997) Mol. Cell. Biol. 17(9):5097–5105; and Dreher, et al. (1997) J. Biol. Chem. 272(46); 29364–29371. Examples of radiation inducible promoters include the EGR-1 promoter. Boothman, et al. (1994) volume 138 supplement pages S68–S71. Tissue specific and tumor specific promoters are well known in the art and include promoters active preferentially in smooth muscle (alpha-actin promoter), pancreas specific (Palmiter, et al. (1987) Cell 50:435), liver specific Rovet, et. al. (1992) J. Biol. Chem. 267:20765; Lemaigne, et al. (1993) J. Biol. Chem. 268:19896; Nitsch, et al. (1993) Mol. Cell. Biol. 13:4494), stomach specific (Kovarik, et al. (1993) J. Biol. Chem. 268:9917, pituitary specific (Rhodes, et al. (1993) Genes Dev. 7:913, prostate specific (U.S. Pat. No. 5,698,443, Henderson, et. al. issued Dec. 16, 1997 entitled "Tissue specific viral vectors"), etc. The term "temporal promoters" refers to promoters which drive transcription or the therapeutic transgene at a point later in the viral cycle relative to the promoter controlling expression of the response element and are used in conjunction with viral vector systems. Examples of such temporally regulated promoters include the adenovirus major late promoter (MLP), other late promoters. In the preferred practice of the invention as exemplified herein, the E3 promoter which is strictly dependent on EIA and viral replication. For herpes simplex viruses, examples of temporal promoter include the latent activated promoters.

The term "non-viral vector" refers to an autonomously replicating, extrachromosomal circular DNA molecule, distinct from the normal genome and nonessential for cell survival under nonselective conditions capable of effecting the expression of a DNA sequence in the target cell. Examples of such non-viral vectors include plasmids. Plasmids autonomously replicate in bacteria to facilitate bacterial production, but it is not necessary that such plasmids replicate in the target cell in order to achieve the therapeutic effect. Additional genes, such as those encoding drug resistance, can be included to allow selection or screening for the presence of the recombinant vector. Such additional genes can include, for example, genes encoding neomycin resistance, multi-drug resistance, thymidine kinase, β-galactosidase, dihydrofolate reductase (DHFR), and chloramphenicol acetyl transferase.

The non-viral vector is provided in a non viral delivery system. Examples of non-viral delivery systems used to introduce an exogenous nucleotide sequence to a target cell include expression plasmids capable of directing the expression of the therapeutic gene of interest in the target cell. The expression plasmid containing the therapeutic gene may be encapsulated in liposomes. The term "liposomes" includes emulsions, foams, micelles, insoluble monolayers, liquid crystals, phospholipid dispersions, lamellar layers and the like. The delivery of nucleotide sequences to target cells using liposome carriers is well known in the art. A variety of methods are available for preparing liposomes, as described in, e.g., Szoka et al. Ann. Rev. Biophys. Bioeng. 9:467 (1980), Szoka, et al. U.S. Pat. No. 4,394,448 issued Jul. 19, 1983, as well as U.S. Pat. Nos. 4,235,871, 4,501,728, 4,837,028, and 5,019,369, incorporated herein by reference. Liposomes useful in the practice of the present invention may be formed from one or more standard vesicle-forming lipids, which generally include neutral and negatively charged phospholipids and a sterol, such as cholesterol. Examples of such vesicle forming lipids include DC-chol, DOGS, DOTMA, DOPE, DOSPA, DMRIE, DOPC, DOTAP, DORIE, DMRIE-HP, n-spermidine cholesterol carbamate and other cationic lipids as disclosed in U.S. Pat. No. 5,650,096. The selection of lipids is generally guided by consideration of, e.g., liposome size, acid lability and stability of the liposomes in the blood stream. Additional components may be added to the liposome formulation to increase serum half-life such as polyethylene glycol coating (so called "PEG-ylation") as described in U.S. Pat. No. 5,013,556 issued May 7, 1991 and U.S. Pat. No. 5,213,804 issued May 25, 1993. In order to insure efficient delivery of the therapeutic gene to a particular tissue or organ, it may be advantageous to incoporate elements into the non-viral delivery system which facilitate cellular targeting. For example, a lipid enacpulated expression plasmid may incorporate modified surface cell receptor ligands to facilitate targeting. Although a simple liposome formulation may be administered, the liposomes either filled or decorated with a desired composition of the invention of the invention can delivered systemically, or can be directed to a tissue of interest, where the liposomes then deliver the selected therapeutic/immunogenic peptide compositions. Examples of such ligands includes antibodies, monoclonal antibodies, humanized antibodies, single chain antibodies, chimeric antibodies or functional fragments (Fv, Fab, Fab') thereof. Alternatively, the DNA constructs of the invention can be linked through a polylysine moiety to a targeting moiety as described in Wu, et al. U.S. Pat. No. 5,166,320 issued Nov. 24, 1992 and Wu, et al., U.S. Pat. No. 5,635,383 issued Jun. 3, 1997, the entire teachings of which are herein incorporated by reference.

The term viral vector refers to a virus comprising a p53 expression cassette. The term "virus" refers to any of the obligate intracellular parasites having no protein-synthesizing or energy-generating mechanism. The viral genome may be RNA or DNA contained with a coated structure of protein of a lipid membrane. The terms virus(es) and viral vector(s) are used interchangeably herein. The viruses useful in the practice of the present invention include recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. The viruses may be naturally occurring viruses or their viral genomes may be modified by recombinant DNA techniques to include expression of exogenous transgenes and may be engineered to be replication deficient, conditionally replicating or replication competent. Chimeric viral vectors which exploit advantageous elements of each of the parent vector properties (See e.g., Feng, et al. (1997) Nature Biotechnology 15:866–870) may also be useful in the practice of the present invention. Minimal vector systems in which the viral backbone contains only the sequences need for packaging of the viral vector and may optionally include a transgene expression cassette may also be produced according to the practice of the present invention. Although it is generally favored to employ a virus from the species to be treated, in some instances it may be advantageous to use vectors derived from different species which possess favorable pathogenic features. For example, equine herpes virus vectors for human gene therapy are described in WO98/27216 published Aug. 5, 1998. The vectors are described as useful for the treatment of humans as the equine virus is not pathogenic to humans. Similarly, ovine adenoviral vectors may be used in human gene therapy as they are claimed to avoid the antibodies against the human adenoviral vectors. Such vectors are described in WO 97/06826 published Apr. 10, 1997.

In the preferred practice of the invention, the viral vector is an adenovirus. The term "adenovirus" is synonomous with the term "adenoviral vector" and refers to viruses of the genus adenoviridiae. The term adenoviridiae refers collectively to animal adenoviruses of the genus mastadenovirus including but no limited to human, bovine, ovine, equine, canine, porcine, murine and simian adenovirus subgenera. In particular, human adenoviruses includes the A–F subgenera as well as the individual serotypes thereof the individual serotypes and A–F subgenera including but not limited to human adenovirus types 1, 2, 3, 4, 4a, 5, 6, 7, 8, 9, 10, 11 (Ad11A and Ad 11P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. The term bovine adenoviruses includes but is not limited to bovine adenovirus types 1,2,3,4,7, and 10. The term canine adenoviruses includes but is not limited to canine types 1 (strains CLL, Glaxo, RI261, Utrect, Toronto 26–61) and 2. The term equine adenoviruses includes but is not limited to equine types 1 and 2. The term porcine adenoviruses includes but is not limited to porcine types 3 and 4. The term viral vector includes replication deficient, replication competent and conditionally replicating viral vectors.

The term "replication deficient" refers to vectors which are incapable of replication in a wild type mammalian cell. In order to produce such vectors in quantity, the producer cell line must be cotransfected with a helper virus or modified to complement the missing functions. E.g. 293 cells have been engineered to complement adenoviral E1 deletions allowing propagation of the E1 deleted replication deficient adenoviral vectors in 293 cells. See Graham, et al. (1977) J. Gen. Virol. 38:59.

The term "replication competetnt viral vectors" refers to a viral vector which is capable of infection, DNA replication, assembly and packaging within an infected cell. The term "conditionally replicating viral vectors" is used herein to refer to replication competent vectors which are designed to achieve selective expression in particular cell types while avoiding untoward broad spectrum infection. Examples of conditionally replicating vectors are described in Bischoff, et al. (1996) Science 274:373–376; Pennisi, E. (1996) Science 274:342–343; Russell, S. J. (1994) Eur. J. of Cancer 30A(8):1165–1171.

Cell type specificity or cell type targeting may also be achieved in viral vectors derived from viruses having characteristically broad infectivities by the modification of the viral envelope proteins. For example, cell targeting has been achieved with adenovirus vectors by selective modification of the viral genome knob and fiber coding sequences to achieve expression of modified knob and fiber domains having specific interaction with unique cell surface receptors. Examples of such modifications are described in Wickham, et al. (1997) J. Virol 71(11):8221–8229 (incorporation of RGD peptides into adenoviral fiber proteins); Arnberg, et al. (1997) Virology 227:239–244 (modification of adenoviral fiber genes to achieve tropism to the eye and genital tract); Harris and Lemoine (1996) TIG 12(10):400–405; Stevenson, et al. (1997) J. Virol. 71(6):4782–4790; Michael, et al. (1995) gene therapy 2:660–668 (incorporation of gastrin releasing peptide fragment into adenovirus fiber protein); and Ohno, et al. (1997) Nature Biotechnology 15:763–767 (incorporation of Protein A-IgG binding domain into Sindbis virus). Other methods of cell specific targeting have been achieved by the conjugation of antibodies or antibody fragments to the envelope proteins (see, e.g. Michael, et al. (1993) J. Biol. Chem 268:6866–6869, Watkins, et al. (1997) gene therapy 4:1004–1012; Douglas, et al. (1996) Nature Biotechnology 14: 1574–1578. Alternatively, particular moieties may be conjugated to the viral surface to achieve targeting (See, e.g. Nilson, et al. (1996) gene therapy 3:280–286 (conjugation of EGF to retroviral proteins). These targeting modifications may be introduced into the viral vectors of the present invention in addition to or in combination with other modifications to the viral genome. Targeting modifications may be used with replication deficient, replication competent or conditionally replicating viruses.

In the preferred practice of the invention as exemplified herein, the preferred vector is derived from the genus adenoviridae. More preferred are vectors derived from human adenovirus types 2 and 5. These vectors may incorporate particular modifications to enhance their therapeutic potential. For example they may include deletions of E1a and E1b genes. Certain other regions may be enhanced or deleted to provide specific features. For example upregulation of the E3 region is described to reduce the immunogenicity associated with human adenoviral vectors administered to human subjects. The E4 region has been implicated as important to expression of transgenes from the CMV promoter, however the E4orf 6 protein has been described as leading to the degradation of p53 in target cells in the presence of E1b large protein. Steegenga, et al. (1998) Oncogene 16:345–347. Consequently, the elimination of such sequences from p53 gene therapy using adenoviral vectors. In the most preferred practice of the invention as exemplified herein, p53 is administered in a viral vector delivery system in the ACN53 vector (described in Wills, et al. (1994) Human Gene Therapy 5:1079–1088).

The term "p53 protein therapy refers to the administration of p53 protein sequence to a cell in such pharmaceutical formulations to effect the intracellular delivery of an active form of the protein to the cell and to exert its cell regulatory effects therein. The term "protein delivery system" refers to 53 protein formulation for the intracellular delivery of the p53 protein to the target cell. Protein delivery systems comprise the therapeutic protein admixed with conventional carriers and excipients which stabilize and/or facilitate the uptake of the protein in the target cell.

The "calpain inhibitor" (abbreviated "CI") refers to a compound which inhibits the proteolytic action of calpain-I, e.g. $\mu$-calpains. The term calpain inhibitors as used herein includes those compounds having calpain I inhibitory activity in addition to or independent of their other biological activities. A wide variety of compounds have been demonstrated to have activity in inhibiting the proteolytic action of calpains. Examples of calpain inhibitors are useful in the practice of the present invention include N-acetyl-leu-leu-norleucinal also known as "calpain inhibitor 1." Additional calpain inhibitors are described in the following United States patents, herein incorporated by reference, U.S. Pat. No. 5,716,980 entitled Alcohol or aldehyde derivatives and their use; U.S. Pat. No. 5,714,471 entitled Peptide and peptide analog protease inhibitors; U.S. Pat. No. 5,693,617 entitled Inhibitors of the 26s proteolytic complex and the 20s proteasome contained therein; U.S. Pat. No. 5,691,368 entitled Substituted oxazolidine calpain and/or cathepsin B inhibitors; U.S. Pat. No. 5,679,680 entitled. $\alpha$.-substituted hydrazides having calpain inhibitory activity; U.S. Pat. No. 5,663,294 entitled Calpain-inhibiting peptide analogs of the kininogen heavy chain; U.S. Pat. No. 5,661,150 entitled Drug for neuroprotection; U.S. Pat. No. 5,658,906 entitled Cysteine protease and serine protease inhibitors; U.S. Pat. No. 5,654,146 entitled Human ice homolog; U.S. Pat. No. 5,639,783 entitled Ketone derivatives; U.S. Pat. No. 5,635,178 entitled Inhibition of complement mediated inflammatory response using monoclonal antibodies specific for a component forming the C56-9 complex which inhibit the platelet or endothelial cell activating function of the C56-9 complex; U.S. Pat. No. 5,629,165 Neural calcium-activated neutral proteinase inhibitors; U.S. Pat. No. 5,622,981 entitled Use of metabotropic receptor agonists in progressive neurodegenerative diseases; U.S. Pat. No. 5,622,967 entitled Quinolone carboxamide Calpain inhibitors; U.S. Pat. No. 5,621,101 entitled Protein kinase inhibitors for treatment of neurological disorders; U.S. Pat. No. 5,554,767 entitled Alpha-mercaptoacrylic acid derivatives having calpain inhibitory activity; U.S. Pat. No. 5,550,108 entitled Inhibition of complement mediated inflammatory response; U.S. Pat. No. 5,541,290 entitled Optically pure calpain inhibitor compounds; U.S. Pat. No. 5,506,243 entitled Sulfonamide derivatives; U.S. Pat. No. 5,498,728 entitled Derivatives of L-tryptophanal and their use as medicinals; U.S. Pat. No. 5,498,616 entitled Cysteine protease and serine protease inhibitors; U.S. Pat. No. 5,461,146 entitled Selected protein kinase inhibitors for the treatment of neurological disorders; U.S. Pat. No. 5,444,042 entitled Method of treatment of neurodegeneration with calpain inhibitors; U.S. Pat. No. 5,424,325 entitled aminoketone derivatives; U.S. Pat. No. 5,422,359 entitled $\alpha$.-aminoketone derivatives; U.S. Pat. No. 5,416,117 entitled Cyclopropenone derivatives; U.S. Pat. No. 5,395,958 entitled Cyclopropene derivatives; U.S. Pat. No. 5,340,922 entitled Neural calcium-activated neutral proteinase inhibitors; U.S. Pat. No. 5,336,783 entitled Calpain inhibitor cystamidin A and its production; U.S. Pat. No. 5,328,909 entitled Cyclopropenone derivatives; and U.S. Pat. No. 5,135,916 entitled Inhibition of complement mediated inflammatory response.

The apoptotic effect of the co-administration of p53 and a calpain inhibitor (CI-1) was investigated in the tumor cell lines decribed in Table 1 below.

TABLE 1

Cell Lines and p53 Status

| Cell line | Source | p53 status |
|---|---|---|
| SK-Hep1 | hepatocellular carcinoma | wildtype |
| HLF | hepatocellular carcinoma | mutated |
| RKO | colorectal | wildtype |
| DLD | colorectal | mutated |
| Hep3B | hepatocellular carcinoma | null |
| U87 | glioblastoma | wildtype |
| A549 | lung | wildtype |
| NCI-H596 | lung | mutated |
| HeLa | cervical carcinoma | wildtype |

P53 was administered to the cells by the use of the replication defective adenoviral vector ACN53 described in Wills, et al., supra. The effect of varying concentrations of rAd-p53 (from $1 \times 10^9$ to $2 \times 10^9$ rAd-p53 particles/ml of solution) was investigated in combination with CI-1 in a range of 5–20 $\mu$m. The effects of individual and combination treatment was determined in the in DLD1, RKO, HLF and SK-Hep1 cells was investigated in substantial accordance with the teaching of Examples 2 and 3 herein. The percentage of apoptotic cells was determined at 17 hours post treatment (with the exception of U87 cells (24 hours) and HeLa cells (68 hours)) with annexin V positive staining. The results are presented in graphical format in FIG. 3 of the attached drawings. In brief, the results were as follows:

TABLE 2

Percentage of Cells Undergoing Apoptosis in Response to Treatment with Calpain Inhibitor Alone or In Combination with rAd-p53

| Cell Line | Control (ZZCB) | 10 $\mu$M CI-1 | $1 \times 10^9$ ACN53 | $1 \times 10^9$ ACN53 + 5 $\mu$M CI-1 | $1 \times 10^9$ ACN53 + 10 $\mu$M CI-1 |
|---|---|---|---|---|---|
| DLD | 8% | 15% | 11% | 39% | 57% |
| HeLa | 4% | 8.3% | 25% [$2 \times 10^9$] | — | 45% |

TABLE 2-continued

Percentage of Cells Undergoing Apoptosis in Response to Treatment with Calpain Inhibitor Alone or In Combination with rAd-p53

| Cell Line | Control (ZZCB) | 10 μM CI-1 | 1 × 10⁹ ACN53 | 1 × 10⁹ ACN53 + 5 μM CI-1 | 1 × 10⁹ ACN53 + 10 μM CI-1 |
|---|---|---|---|---|---|
| RKO | 10% | 13% [20 μM] | 11% | 41% | 67% |
| HLF | 7% | 7% | 12% | 20% | 48% |
| SK-Hep1 | 9% | 11% [5 μM] | 16% [2 × 10⁹] | 70% | — |
| U87 | 23% (24 hrs) | 41% | 30% | — | 83% |

In each of the above experiments, an empty cassette control virus (ZZCB) was used to assess the transgene specific effect of the rAd-p53 vector. In each instance, there was no significant increase in apoptosis beyond that seen with CI-1 alone demonstrating a specific transgene effect, and not a non specific viral effect. This data demonstrates that CI-1 in combination with rAd-p53 results in a significant enhancement to the apoptotic effects of p53 beyond that seen with either CI-1 or rAd-p53 alone. Notably, the effects were seen in p53 mutated, p53 null and p53 wildtype cells. The data presented demonstrates a multiplicative rather than additive effect of the combined treatment.

Calpains have been shown to play a role in p53 stability. (Gonen et al., 1997; Kubbutat and Vousden, 1997). In targeting p53 for degradation, $\mu$-calpains, and to a much lesser extent milli-calpains, reportedly recognize the tertiary structure of the protein and preferentially cleave wildtype p53 at a single cleavage site located at the N-terminal region overlapping the mdm-2 binding site (Kubbutat and Vousden, 1997). Deletion of the calpain consensus cleavage site in p53 has been shown to inhibit the ability of mdm-2 to bind to p53 resulting in an increase in p53 half-life. Deletion of the calpain consensus cleavage site does not eliminate the transactivational and apoptotic functions of p53. (Kubbutat et al., 1997). Inhibition of proteosomes by calpain inhibitors has been shown to lead to increased levels of p53, and apoptosis in the MOLT-4 cell line (Shinohara et al., 1996).

Figure 5:
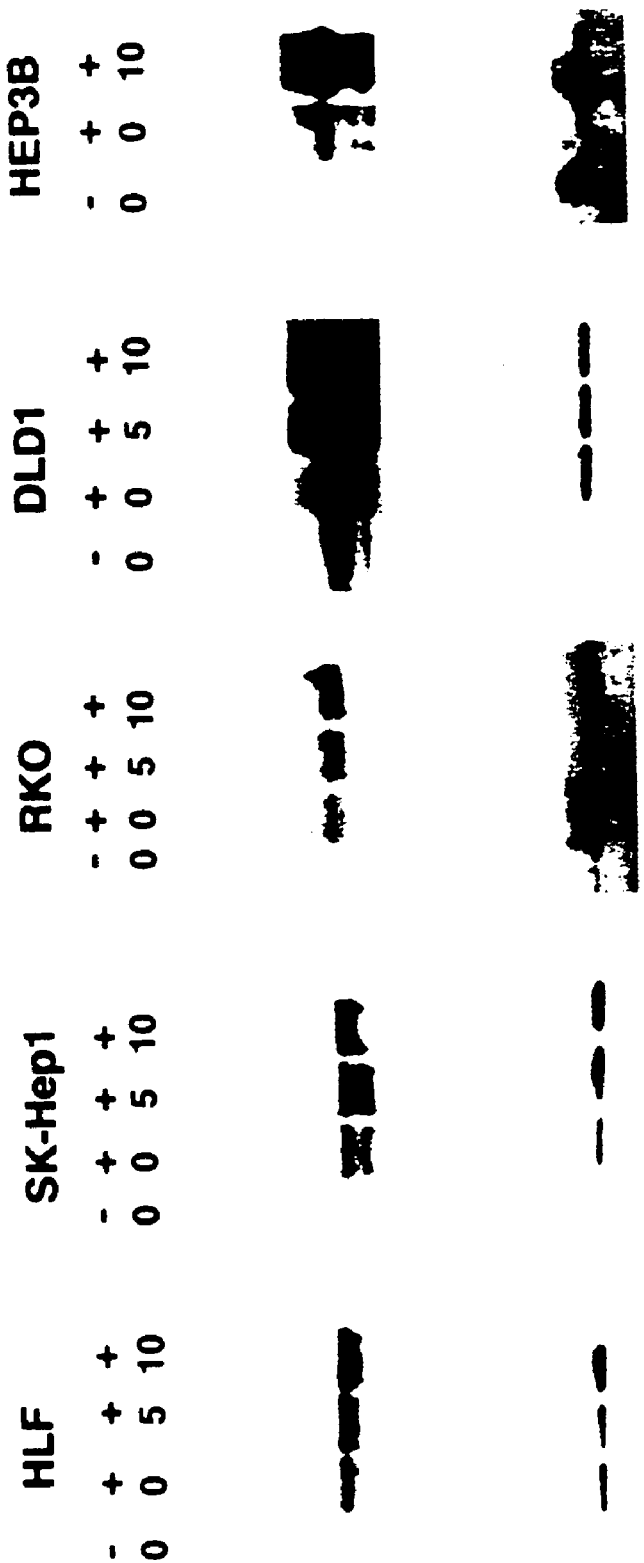
FIG. 5 contains the results of Western blots measuring the levels of p53 and p21 in rAd-p53 infected cells in the presence of varying concentrations of CI-1. Above each lane is a "+" of "−" which indicates if the cells were pulsed with 1×10$^9$ rAd-p53 for one hour (+) or not (−). The row of numbers below indicates the $\mu$M concentration of CI-1 to which the cells were exposed at 17 hours post-infection. The upper row of chemiluminescent signals provides the levels of p53 while the lower row of chemiluminescent signals provides the levels of p21. As indicated by the data presented, in response to 1×10$^9$ particle/ml rAd-p53 at 17 hours post-infection, HLF cells showed the increases in p53 and p21 protein levels. When 5 $\mu$M CI-1 was added with rAd-p53, the levels of p53 increased two fold, as quantitated on NIH imaging. When 10 $\mu$M CI-1 was added, the levels of p53 and p21 increased approximately three fold. Similar results were seen with the cell lines SK-Hep1 and DLD1. The cell line RKO showed a two fold increase in p53 and p21 levels in response to 5 $\mu$M CI-1, while a higher increase in p53 levels at 10 $\mu$M CI-1 was seen, about a five fold increase over rAd-p53 alone.
Figure 6:
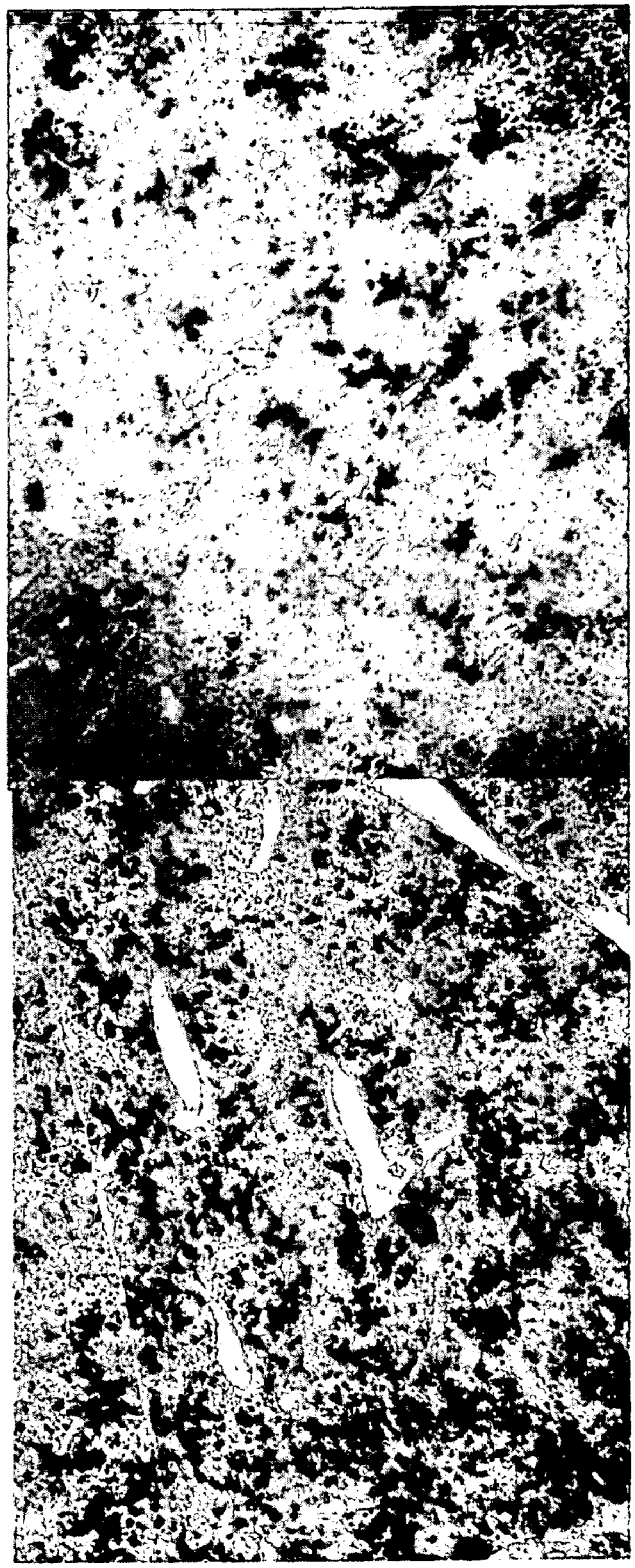
FIG. 6 are microscopic photographs (5 days post treatment) of 10 micron X-gal stained cross sections from livers of C57 BL/6 mice sacrificed 3 days post infection with a recombinant adenoviral vector expressing the β-galactosidase marker gene (BGCG) in combination with 120 mg/kg of CI-1 (Panel A) and BGCG alone (Panel B). CI-1 was intraperitoneally administered on days 1, 2, and 3. BGCG (rAd-b-gal) was admistered by tail vein injection on day 2.

To determine if increases in exogeneous p53 levels occurred in response to CI-1, the p53 null cell line Hep3B was infected with 1×10⁹ particle/ml and assayed for p53 protein levels by western blots 17 hours post-infection. The results are shown in FIG. 5. No p53 protein was detected in untreated Hep3B. p53 protein was detected in cells infected with rAd53 alone, and increased greater then 10 fold when infected with rAd-p53 in the presence of 10 μM calpain inhibitor 1. The results presented in FIG. 5 demonstrate a 2–5x increase in p53 levels in response to calpain inhibitor 1 in cell lines with endogenous wildtype and mutated p53 status. The enhancement of p53 stability by CI-1 may not, therefore, be the sole mechanism by which enhanced cell death has been achieved. This result also suggests that CI-1 stabilizes exogenous as well as endogenous p53, and was confirmed using a p53 null cell line, Hep3B. Thus, a new mechanism of action is involved other than p53 stability in the increased induction of apoptosis by the combination of CI-1 and p53.

Figure 4:
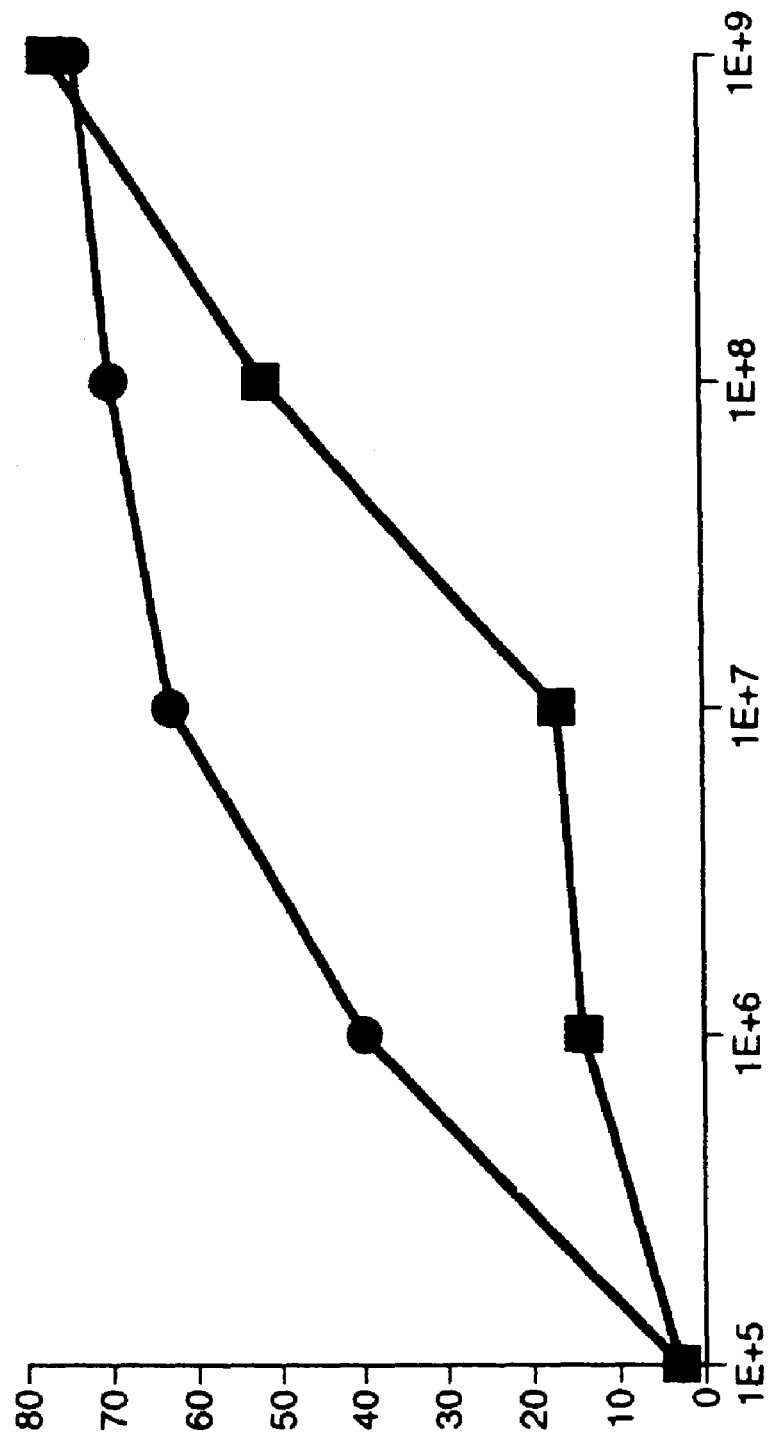
FIG. 4 is a graphical representation of the percent annexin V postive HLF cells (apoptotic cells) as a function of increasing dosage of rAd-p53 alone (■), and rAd-p53 in combination with 10 $\mu$M CI-1 (●). The horizontal axis represents the concentration in units of [number of particles of rAd-p53/milliliter of solution]. The vertical axis represents the percent of annexin V positive (apoptotic) cells as determined by flow cytometry.

To quantitate the increased efficacy of rAd-p53 induced cell killing in tumor cell lines in response to CI-1 treatment, HLF cells were infected with increasing concentrations of rAd-p53 with or without 10 μM CI-1, and assayed for percentage apoptotic cells by annexin V-FITC staining 42 hours post-treatment in substantial accordance with the teaching of Example 3 herein. A dosage response curve was plotted and is shown in FIG. 4. Untreated cells and cells treated with 10 μM CI-1 alone showed low background annexin V staining (2–3% respectively). No increase in annexin V-FITC positive cells was detected at 1×10⁵ particles/ml rAd-p53 with or without 10 μM CI-1. At 1×10⁶ particles/ml rAd-p53, the percentage apoptotic cells without CI-1 was 14%, while 40% of annexin V positive cells was detected when cell were treated with 10 μM CI-1. At a concentration of 1×10⁷ ACN53 particles/ml, 17% annexin V positive without and 63% with 10 μM CI-1 was detected. At 1×10⁸ particles/ml, 52% were annexin V positive without and 70% positive with inhibitor treatment. At a dose of 1×10⁹ particles of rAd-p53, however, the percentage annexin V positive was about the same for both 77% without and 74% with 10 μM CI-1. A 1×10⁹ particle/ml concentration of rAd-p53 was sufficient to induce approximately 50% cell death, while only a 1×10⁷ particle/ml concentration rAd-p53 was needed to induce approximately the same percentage of cell death when 10 μM CI-1 as added. These results demonstrate an approximately two log decrease in the particles/ml of rAd-p53 needed to induce approximately 50% cell death in response to treatment with 10 μM CI-1 at 42 hours.

B: Micro-Calpain Inhibitors Induce Apoptosis in P53 Positive Tumors:

The present invention provides a method to enhance apoptosis in a cell by the administration of p53 in combination with a calpain inhibitor.

The term "p53 positive" refers to the genotype of a cell which possesses at least one copy of a gene encoding a functional p53 molecule. p53 positive is distinguished from p53 negative which refers to the geneotype of a cell which does not possess at least one copy of a gene encoding a functional p53 molecule.

Although many human tumors are p53 deficient, a significant number of tumors are p53 positive. Without being bound to any particular mechanism of action, we believe that the p53 produced in p53 positive tumor cells is of insufficient concentration to induce apoptosis. Therefore, the adminstration of agents which enhance the effective concentration of p53 in p53 positive tumor cells would permit the endogenous p53 to exert its therapeutic effect. The present invention provides a method of inducing p53 mediated apoptosis in a p53 positive cell by the adminsitration of a calpain inhibitor.

The effect of an inhibitor of $\mu$-calpains, CI-1 (N-acetyl-leu-leu-norleucinal), was investigated for its ability to enhance p53 mediated apoptosis in tumor cell lines having p53+ and p53− status listed in Table1. Each cell line was treated with 5–50 μM CI-1 for 17–26 hours. To detect a G0/G1 block, bromodeoxyuridine (BrdU) incorporation followed by flow cytometric analysis was done 17 hours post-treatment as described in Example 4 herein. In response to 17 hours of treatment, bromodeoxyuridine labeling showed wildtype, but not mutated p53 cell lines arrested in G0/G1. Annexin V-FITC and propidium iodide staining (as more fully described in Example 3 herein) was then used to determine if the cells were induced to apoptosis. Wildtype p53 tumor cell lines, but not mutated or null, were sensitive to CI-1 induced apoptosis, as assayed 26 hours post-treatment by annexin V-FITC and propidium iodide staining, suggesting activation of a p53 dependent apoptotic pathway in response to CI-1 treatment. The results of these experiments are presented in FIGS. 1 and 2 of the attached drawings. In FIG. 1, each point on the graph represents percentage annexin V positive after background percentage (DMF alone) was subtracted. The results of these experiments is presented in Table 3 below;

TABLE 3

Percent Annexin V Positive Staining; 26 hours post treatment (HeLa 44 hours)

| [CI-1] | HLF | SK-Hep-1 | RKO | A549 | Hep3B | HeLa | DLD-1 |
|---|---|---|---|---|---|---|---|
| 0 | 12 | 20 | 10 | 5 | 30 | 39 | 8 |
| 10 | 27 | 32 | 13 | 6 |  | 28 | 15 |
| 20 | 27 | 66 | 33 | 5 | 36 | 48 | 17 |
| 30 | 33 | 73 |  |  |  | 55 | 17 |
| 40 | 20 | 75 |  |  |  | 67 |  |
| 50 | 21 | 73 | 57 | 18 | 32 | 80 | 18 |

The data presented above demonstrates that at 26 hours post-treatment with CI-1, p53 wildtype tumor cells demonstrated a significant increase in the percentage of cells undergoing apoptosis in contrast to the p53 mutated and null tumor cells. The data presented demonstrates an increasing dose response with increasing concentrations of CI-1. At 20 μM concentration, the increase in the percent of cells annexin V positive over background staining became more significant in cells with p53 wildtype status. SK-Hep1 cells increased the percentage of annexin V positive cells from background staining of 20% to 66%. In RKO cells, an increase from 10% to 52% cells annexin V positive cells was seen. HLF increased from a background staining of 12% to 27% and DLD-1 increased from 8% to 11%. At the highest concentration, 50 μM, SK-Hep1 increased annexin V positive cell to 73%, RKO to 61%, while DLD1 increased to 23%, and HLF to 21%. The hepatocellular carcinoma cell line with null p53 status, Hep3B, (FIG. 1) showed no increase in the percentage of apoptotic cells in response to even the highest concentration of inhibitor (50 μM). Other cell lines treated with CI-1 included the p53 wild type glioblastoma cell line U87, which showed an increase in the percentage of apoptotic cells from 5% to 72% in response to 20 μM CI-1 treatment. When U87 cells were treated with a lower concentration of calpain inhibitor 1, 10 μM for 4 days, nearly 100% of cells were annexin V-FITC positive. The lung cell line with p53 mutated status, NCI-H596 showed no increase in the percent of cells annexin V positive in response to treatment. HeLa cells, which have E6 mediated degradation of p53, were induced to apoptosis with higher concentrations of CI-1.

The use of an inhibitor more specific for inactivation of milli-calpains, calpain inhibitor 2, showed no significant effect on the induction of apoptosis in combination with rAd-p53 in HLF cells at 10 μM (6% untreated to 22% rAd-p53 treated to 28% rAd-p53+10 μM CI-1). At higher concentrations (150 μM), where this inhibitor has been shown to inactivate 1-calpains, there was 64% annexin V-FITC positive cells were treated with 150 micromolar CI-2 and infected with rAd-p53 as compared with 22% for rAd-p53. In a cell line with endogenous wildtype p53, SK-Hep1, treatment with calpain inhibitor 2 at 20 μM gave no significant increase in annexin V-FITC positive cells (See FIG. 3), in contrast to treatment with calpain inhibitor 1 shown above. (Sources and protocols are provided in the Examples below).

Figure 2:
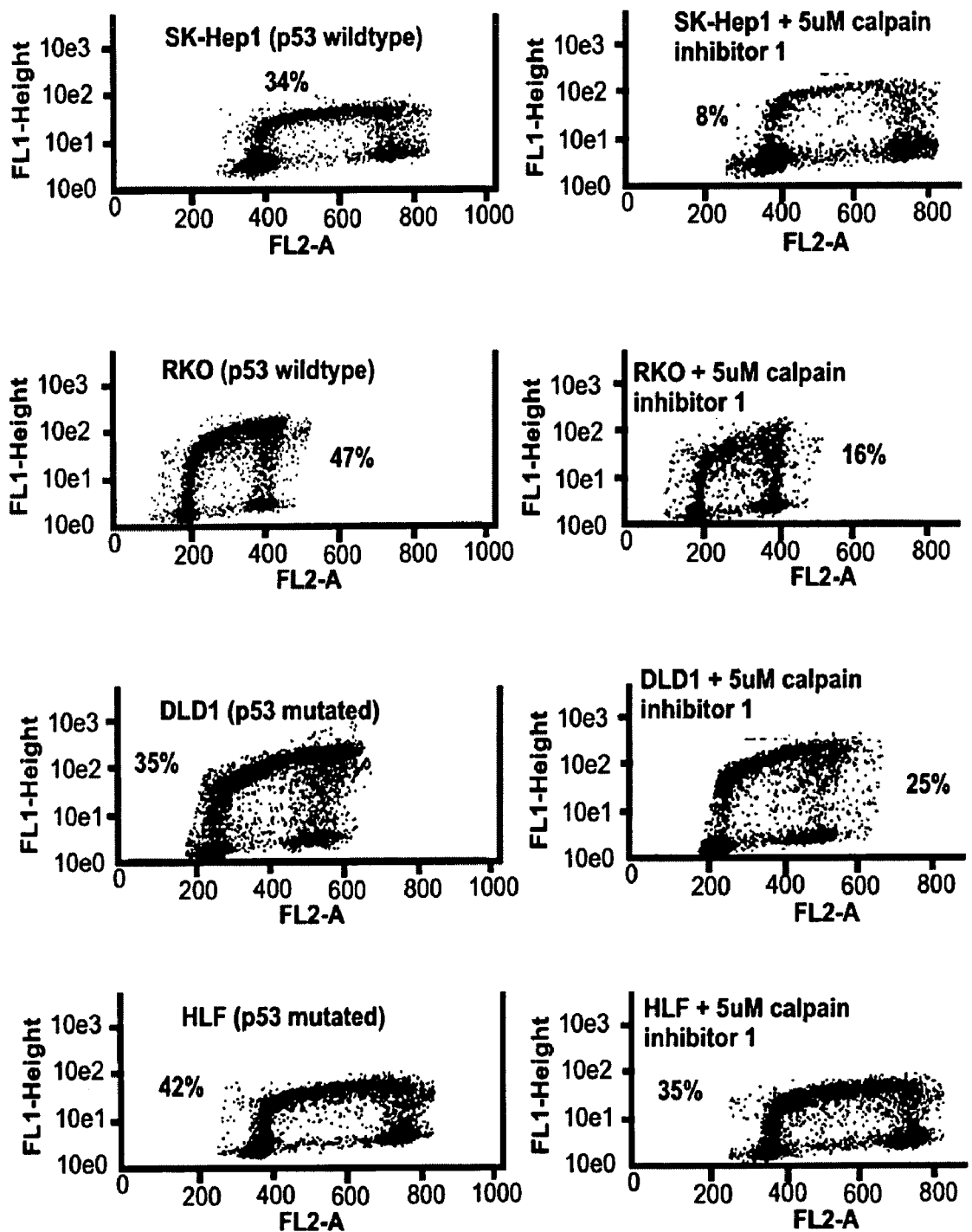
FIG. 2 are the results of flow cytometry experiments comparing the amount of BrdU labelling of cells to detect a G0/G1 arrest in response to calpain inhibitor 1 treatment in cell lines which differ in endogeneous p53 status. Two colorectal (RKO and DLD1) and two hepatocellular carcinoma cell lines (SK-Hep1 and HLF) which differ in endogenous p53 status showing BrdU labelling in response to DMF alone versus 5 $\mu$M CI-1 for 17 hours.

Increased activity of p53 in response to calpain inhibitor 1 treatment was detected by the ability of cell lines with wildtype p53 status to arrest in G0/G1. The hepatocellular carcinoma cell line with p53 mutated status, HLF, treated with the solvent DMF alone showed 42% of the cells incorporating BrdU label after a 2 hour pulse time (FIG. 2). In response to 5 μM CI-1, 35% of the cells were incorporating BrdU label (FIG. 2). In contrast, SK-Hep1 cells with wildtype p53 status showed 34% of the control cells incorporating BrdU in response to DMF, while 8% of cells incorporated BrdU label in response to 5 μM CI-1. A colorectal cell line RKO, with p53 wildtype status showed 47% of the control cells incorporating BrdU in response to DMF, while 16% of cells incorporated BrdU label in response to 5 μM CI-1. In contrast, DLD1 cells showed 35% of cells incorporating BrdU without calpain treatment, and upon 5 μM CI-1 treatment for 17 hours, the percentage of cells incorporating BrdU decreased only to about 25%.

C: Micro-Calpain Inhibitors Increase the Infectivity of a Target Cell to Viral Vectors:

It has been observed that the infectivity of cells with respect to a given viral vector varies. The basis for this difference in infectivity is not well understood. In instances where intracellular gene dosage is important, such as in the use of p53 to induce apoptosis, it may be necessary or desirable to increase the infectivity of the cells to the particular vector. Additionally, increasing the infectivity of a cell to the particular vector may permit the use of smaller dosages to achieve similar therapeutic activity, therefore reducing potential side effects of the treatment. The present invention provides a method of increasing the infectivity of a cell to a viral vector by treatment of the cell with a calpain inhibitor.

The term "increasing infectivity" refers to an increase in the ability of a viral vector to infect a cell as measured by an increase in infection transduction efficiency. "Infection Transduction Efficiency" (ITE) will be used herein to describe this value, and is proportional to the probability that the collision of a virus particle will result in the successful expression of the transgene encoded thereby. Only a fraction of the contacts between the adenovirus and the cell surface will result in a successful infection/transduction event. The probability of a virus particle colliding with a cell can be modeled using classical diffusion kinetics. Without providing the distinct mathematical derivation, it can be determine that ITE is described by the equation:

$$ITE = -\ln(1-F)/I \, \phi \, V \, t^{0.5}$$

wherein, F represents the fraction of cells in a given population which are "positive" for the parameter under evaluation (e.g. expression of the virally encoded gene); φ represents the average surface are of the cell; I is a constant proportional to the diffusion coefficient and will be affected by the virus, the viscosity of the solution, etc. and is determined empirically, t is the time of exposure and V is the concentration of particles per unit volume.

The term viral vector is described above with the exception that the expression cassette is not limited to the p53 gene rather includes a therapeutic transgene.

The term "therapeutic transgene" refers to a nucleotide sequence the expression of which in the target cell produces a therapeutic effect. The term therapeutic transgene includes but is not limited to tumor suppressor genes, antigenic genes, cytotoxic genes, cytostatic genes, pro-drug activating genes, apoptotic genes, pharmaceutical genes or anti-angiogenic genes. The vectors of the present invention may be used to produce one or more therapeutic transgenes, either in tandem through the use of IRES elements or through independently regulated promoters.

The term "tumor suppressor gene" refers to a nucleotide sequence, the expression of which in the target cell is capable of supressing the neoplastic phenotype and/or inducing apoptosis. Examples of tumor suppressor genes useful in the practice of the present invention include the p53 gene, the APC gene, the DPC-4 gene, the BRCA-1 gene, the BRCA-2 gene, the WT-1 gene, the retinoblastoma gene (Lee, et al. (1987) Nature 329:642), the MMAC-1/PTEN gene, the adenomatous polyposis coli protein (Albertsen, et al., U.S. Pat. No. 5,783,666 issued Jul. 21, 1998), the deleted in colon carcinoma (DCC) gene, the MMSC-2 gene, the NF-1 gene, nasopharyngeal carcinoma tumor suppressor gene that maps at chromosome 3p21.3. (Cheng, et al. 1998. Proc. Nat. Acad. Sci. 95:3042–3047), the MTS1 gene, the CDK4 gene, the NF-1 gene, the NF2 gene, and the VHL gene.

The term "antigenic genes" refers to a nucleotide sequence, the expression of which in the target cells results in the production of a cell surface antigenic protein capable of recognition by the immune system. Examples of antigenic genes include carcinoembryonic antigen (CEA), p53 (as described in Levine, A. PCT International Publication No. WO94/02167 published Feb. 3, 1994). In order to facilatate immune recognition, the antigenic gene may be fused to the MHC class I antigen.

The term "cytotoxic gene" refers to nucleotide sequence, the expression of which in a cell produces a toxic effect. Examples of such cytotoxic genes include nucleotide sequences encoding pseudomonas exotoxin, ricin toxin, diptheria toxin, and the like.

The term "cytostatic gene" refers to nucleotide sequence, the expression of which in a cell produces an arrest in the cell cycle. Examples of such cytostatic genes include p21, the retinoblastoma gene, the E2F-Rb gene, genes encoding cyclin dependent kinase inhibitors such as P16, p15, p18 and p19, the growth arrest specific homeobox (GAX) gene as described in Branellec, et al. (PCT Publication WO97/16459 published May 9, 1997 and PCT Publication WO96/30385 published Oct. 3, 1996).

The term "cytokine gene" refers to a nucleotide sequence, the expression of which in a cell produces a cytokine. Examples of such cytokines include GM-CSF, the interleukins, especially IL-1, IL-2, IL-4, IL-12, IL-10, IL-19, IL-20, interferons of the $\alpha$, $\beta$, and $\gamma$ subtypes especially interferon $\alpha$-2b and fusions such as interferon $\alpha$-2$\alpha$-1.

The term "chemokine gene" refers to a nucleotide sequence, the expression of which in a cell produces a cytokine. The term chemokine refers to a group of structurally related low-molecular cytokines weight factors secreted by cells are structurally related having mitogenic, chemotactic or inflammatory activities. They are primarily cationic proteins of 70 to 100 amino acid residues that share four conserved cysteine. These proteins can be sorted into two groups based on the spacing of the two amino-terminal cysteines. In the first group, the two cysteines are separated by a single residue (C-x-C), while in the second group, they are adjacent (C—C). Examples of member of the 'C-x-C' chemokines include but are not limited to platelet factor 4 (PF4), platelet basic protein (PBP), interleukin-8 (IL8), melanoma growth stimulatory activity protein (MGSA), macrophage inflammatory protein 2 (MIP-2), mouse Mig (m119), chicken 9E3 (or pCEF-4), pig alveolar macrophage chemotactic factors I and II (AMCF-I and -II), pre-B cell growth stimulating factor (PBSF), and IP10. Examples of members of the 'C—C' group include but are not limited to monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1 $\alpha$ (MIP-1-$\alpha$), macrophage inflammatory protein 1 $\beta$ (MIP-1-$\beta$), macrophage inflammatory protein 1 $\gamma$ (MIP-1-$\gamma$), macrophage inflammatory protein 3 $\alpha$ (MIP-3-$\alpha$, $\alpha$, macrophage inflammatory protein 3$\beta$ (MIP-3-$\beta$), chemokine (ELC), macrophage inflammatory protein 4 (MIP-4), macrophage inflammatory protein 5 (MIP-5), LD78 $\beta$, RANTES, SIS-epsilon (p500), thymus and activation-regulated chemokine (TARC), eotaxin, I-309, human protein HCC-1/NCC-2, human protein HCC-3, mouse protein C10.

The term "pharmaceutical protein gene" refers to nucleotide sequence, the expression of which results in the production of protein have pharmaceutically effect in the target cell. Examples of such pharmceutical genes include the proinsulin gene and analogs (as described in PCT International Patent Application No. WO98/31397, growth hormone gene, dopamine, serotonin, epidermal growth factor, GABA, ACTH, NGF, VEGF (to increase blood perfusion to target tissue, induce angiogenesis, PCT publication WO98/32859 publsihed Jul. 30, 1998), thrombospondin etc.

The term "pro-apoptotic gene" refers to a nucleotide sequence, the expression thereof results in the programmed cell death of the cell. Examples of pro-apoptotic genes include p53, adenovirus E3-11.6K, the adenovirus E4orf4 gene, p53 pathway genes, and genes encoding the caspases.

The term "pro-drug activing genes" refers to nucleotide sequences, the expression of which, results in the production of protein capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine to 5 fluorouracil, a potent antitumor agent). The lysis of the tumor cell provides a localized burst of cytosine deaminase capable of converting 5FC to 5FU at the localized point of the tumor resulting in the killing of many surrounding tumor cells. This results in the killing of a large number of tumor cells without the necessity of infecting these cells with an adenovirus (the so-called bystander effect"). Additionally, the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir may be employed.

The term "anti-angiogenic" genes refers to a nucleotide sequence, the expression of which results in the extracellular secretion of anti-angiogenic factors. Anti-angiogenesis factors include angiostatin, inhibitors of vascular endothelial growth factor (VEGF) such as Tie 2 (as described in PNAS(USA)(1998) 95:8795–8800) and endostatin.

It will be readily apparent to those of skill in the art that modifications and or deletions to the above referenced genes so as to encode functional subfragments of the wild type protein may be readily adapted for use in the practice of the present invention. It will be readily apparent to those of skill in the art that the above therapeutic genes may be secreted into the media or localized to particular intracellular locations by inclusion of a targeting moiety such as a signal peptide or nuclear localization signal (NLS). Also included in the definition of therapeutic transgene are fusion proteins of the therapeutic transgene with the herpes simplex virus type 1 (HSV-1) structural protein, VP22. See, e.g. Elliott, G. & O'Hare, P. Cell. 88:223–233:1997; Marshall, A. & Castellino, A. Research News Briefs. Nature Biotechnology. 15:205:1997; O'Hare, et al. PCT publication WO97/05265 published Feb. 13, 1997. A similar targeting moiety derived from the HIV Tat protein is also described in Vives, et al. (1997) J. Biol. Chem. 272:16010–16017.

Figure 7A:
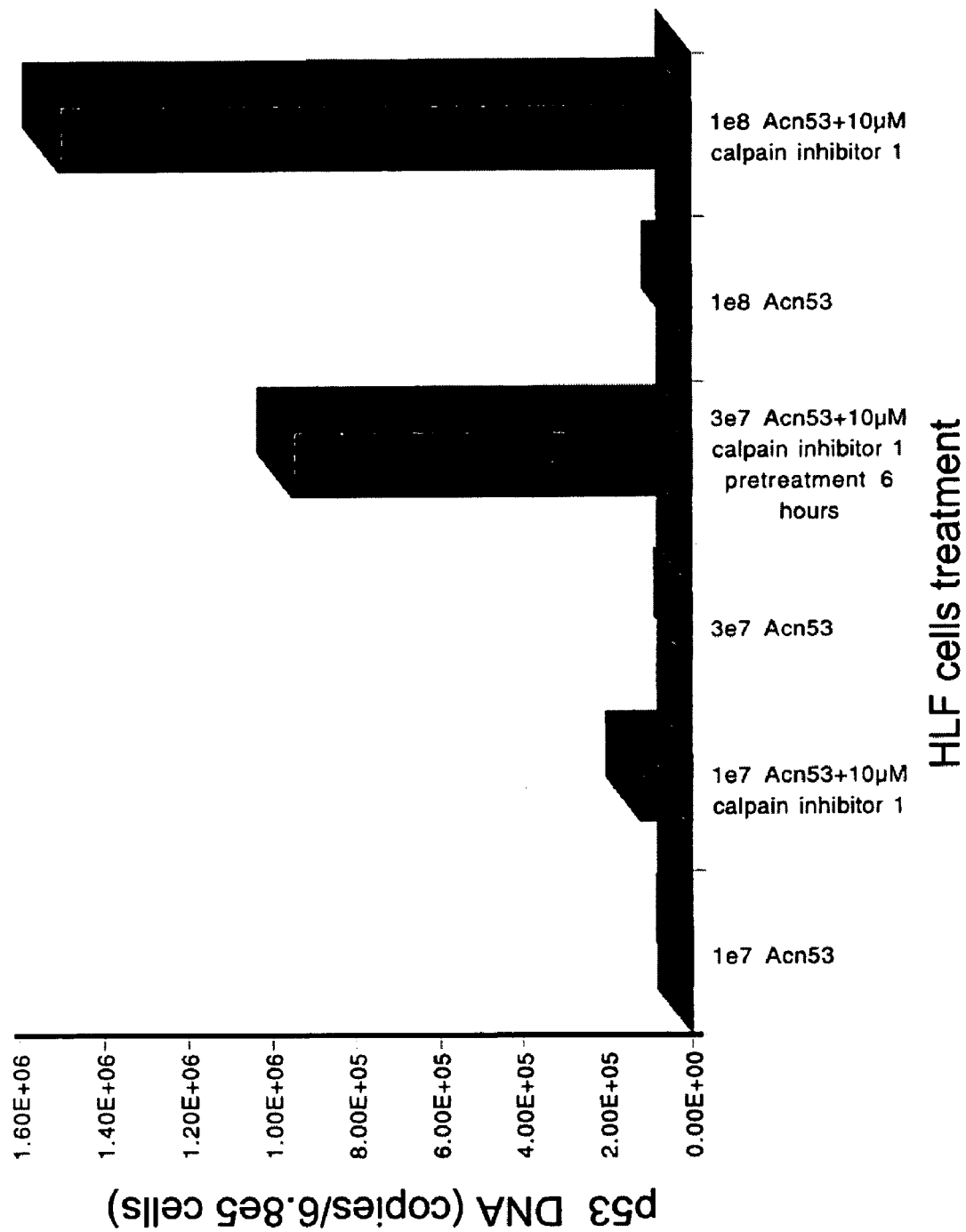
FIG. 7 A and B are histogram graphical representations respectively of the number of viral copies of DNA and transgene RNA per $6.8\times10^5$ HLF cells (as determined by PCR and RT-PCR respectively) in response to treatment in the presence and absence of CI-1. The vertical axis represents the number of copies of p53 DNA detected by PCR (FIG. 7A) and p53 mRNA (FIG. 7B) per $6.8\times10^5$ HLF cells. Column A represents treatment with $1\times10^7$ ACN53 alone. Column B represents treatment with $1\times10^7$ ACN53 in the presence of 10 µM CI-1. Column C represents treatment with $3\times10^7$ ACN53. Column D represents treatment with 10 µM CI-1 for a period of six hours followed by treatment with $3\times10^7$ ACN53. Column E represents treatment with $1\times10^8$ ACN53. Column F represents $1\times10^8$ ACN53 in combination with 10 µM CI-1. Indeed, these experiments indicate that pretreatment of the cells with CI-1 leading to increased apoptosis may be independent of p53 stabilization by the inhibitor and acting through an independent mechanism of action.
Figure 7B:
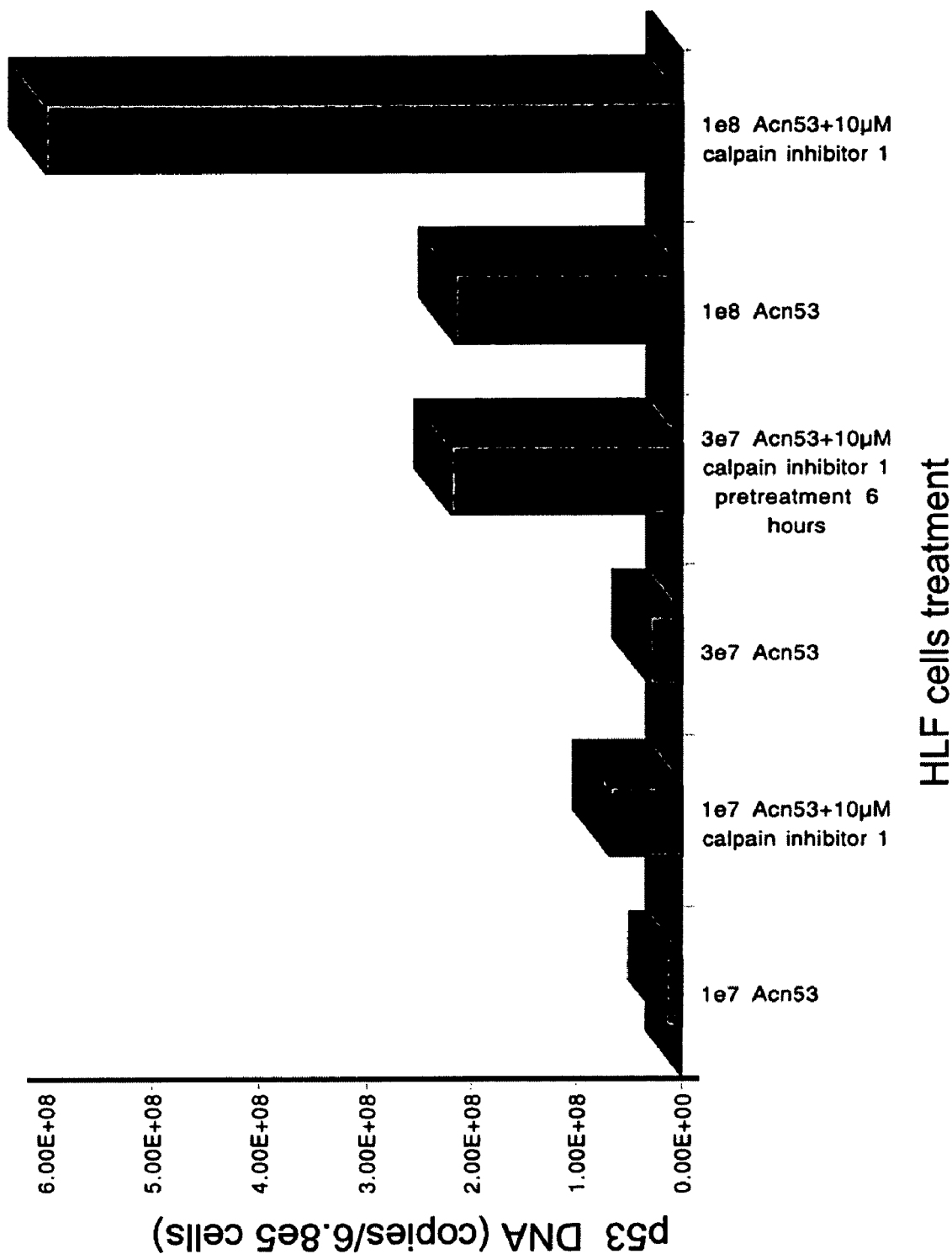

The effects of the use of calpain inhibitors, particularly CI-1, were investigated in their ability to increase the infectivity of the HLF tumor cell line to rAd-p53. HLF cell lines were prepared in substantial accordance with the teaching of example 6 herein. The cells were exposed to two concentrations of rAd-p53 in the presence and absence of 10 $\mu$M CI-1. The total number of copies of rAd-p53 DNA were determined by PCR as described in Example 6. The results of these experiments are presented in Table 4 below and in graphical form in FIG. 7 of the attached drawings.

TABLE 4

Effect of CI-1 on the Infectivity of HLF Cells In Response to Co-Administration with ACN53.

| rAd-53 (particles/ml) | [CI-1] $\mu$M | p53 DNA (copies/6.8 × $10^5$ cells) |
|---|---|---|
| 1 × $10^7$ | 0 | 2.4 × $10^3$ |
| 1 × $10^7$ | 10 | 1.2 × $10^5$ |
| 1 × $10^8$ | 0 | 3.3 × $10^4$ |
| 1 × $10^8$ | 10 | 1.5 × $10^6$ |

As can be clearly seen from the data presented, the introduction of 10 $\mu$M concentration of the calpain inhibitor CI-1 resulted in a 50 fold increase in intracellular viral DNA at a viral concentration of 1×$10^7$ and 1×$10^8$ particles.

A similar experiment was conducted to determine the effect of pre-treatment of the cells with the calpain inhibitor. The cell lines were prepared as indicated above. In this experiment, one group of cells was pretreated with a 10 $\mu$M concentration of CI-1 for a period of 6 hours prior to exposure to the Ad-p53. The control sample was not pretreated. The results of these experiments are presented in Table 5 below and in graphical form in FIG. 7 of the attached drawings.

TABLE 5

Effect of CI-1 on the Infectivity of HLF Cells In Response to 6 Hourt Pre-Treatment with CI-1

| ACN53 (particles/ml) | [CI-1] $\mu$M | p53 DNA (copies/6.8 × $10^5$ cells) |
|---|---|---|
| 3 × $10^7$ | 0 | 6.5 × $10^3$ |
| 3 × $10^7$ | 10 | 9.5 × $10^5$ |

As can be seen from the data presented, the effect of pretreatment of the cells with CI-1 increased the infectivity of the cells to the virus to approximately 130 times that of the untreated cells, as compared without pre-treatment, where the effect was 50 fold higher. Thus, it is preferred that the cells be pretreated with the calpain inhibitor prior to exposure to the viral vector to maximize the infectivity of the cell line to the vector.

Figure 12A:
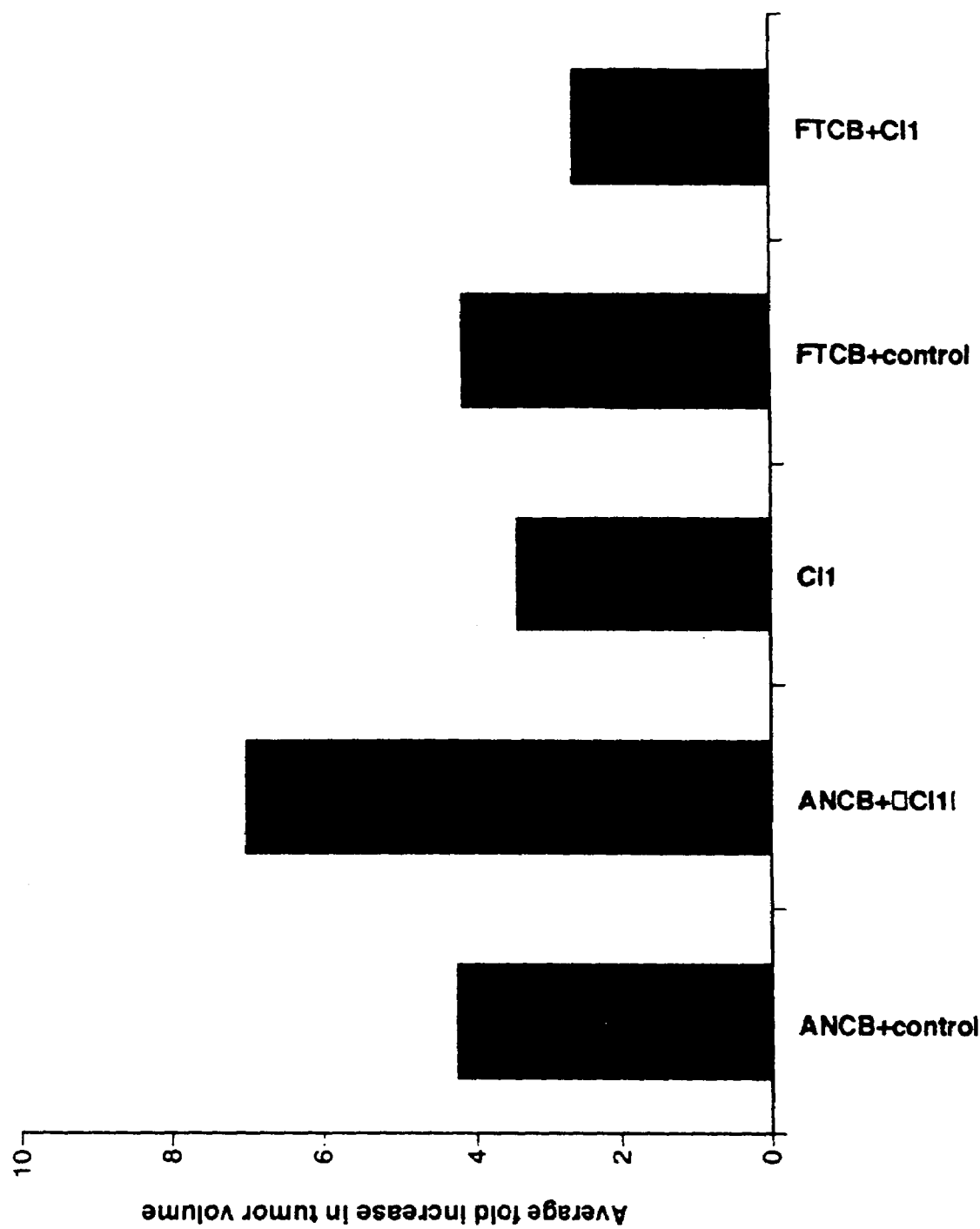
FIGS. 12 A,B and C present the results of an in vivo mouse model following adminsitration of recombinant adenovirus encoding p53 alone or in combination with calpain inhibitors. Tumor growth/regression was evaluated at Day 4, Day 8 and Day 11 post-treatment (FIGS. 12 A,B and C respectively).
Figure 12B:
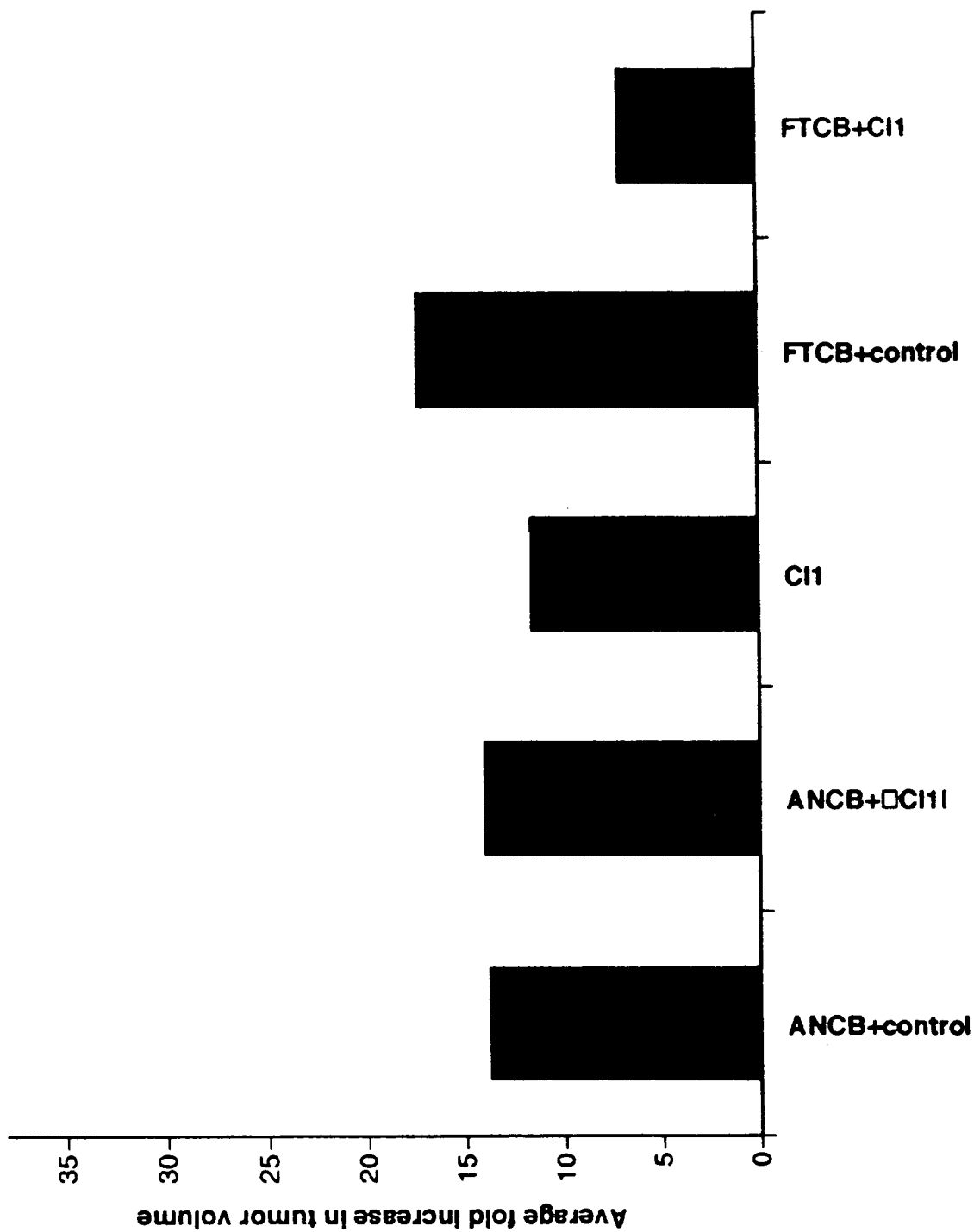
Figure 12C:
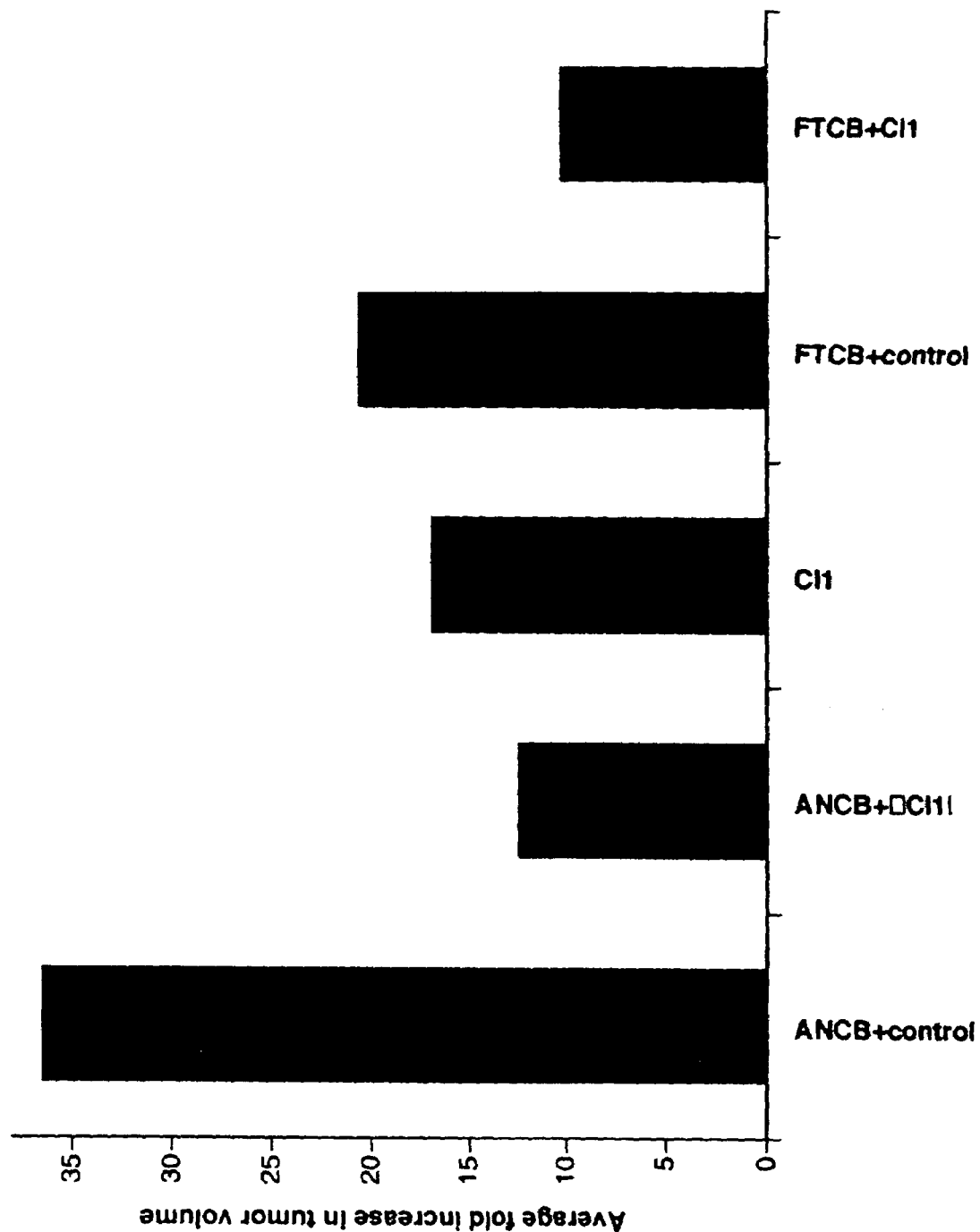

The in vitro results presented above were confirmed in a rodent cancer model. Briefly, healthy immune competent mice were injected with JC (mouse mammary carcinoma, p53 mutant) cells and tumors were permitted to form. This is a particularly rigorous model as JC cells are particularly difficult to infect and the mouse is an immunocompetent mouse capable of producing an immune response to the human adenovirus and/or the human p53 transgene. After 2 weeks, flank tumors were present in all animals. Calpain inhibitor was administered via intraperitoneal injection to a concentration of approximately 60 mg/kg approximately 24 hours prior to administration of the recombinant rAd-p53 virus. Appropriate control viruses and solutions were employed. The mice were injected with 1×$10^{10}$ particles of rAd-p53 per injection intratumorally in combination with intraperitoneally injected CI-1 at a concentration of 60 mg/kg for a period of 5 days, 2 days off and then for 5 more days. Tumor growth/regression was evaluated at Day 4, Day 8 and Day 11 post-treatment (FIGS. 12 A,B and C respectively). In all instances the rate of decrease in tumor growth was at least 40% reduction in fold increase in tumor volume in mice treated with calpain inhibitor 1 in addition to FTCB, in comparison with the mice treated with the FTCB vector alone. It is particularly noteworthy in this instance that calpain inhibitor alone provided significant antitumor effects. Microscopic examination of other organs removed from the animals indicates little or no collateral effects of the administration indicating that non-tumor p53 positive cells were not harmed by the treatment regimen. This model provides demonstrative proof of the use of the compositions and methods of the present invention in the in vivo treatment of cancer.

D. Increase NF-Kappa-B Mediated Transcription of Transgenes

Nuclear Factor Kappa B (NFkB) was initially thought to be active only in B cells where it binds to a specific DNA sequence (GGGGACTTTCC; SEQ ID NO:1) within the immunoglobulin light chain kappa enhancer region in mice and humans. However, later studies have demonstrated that NFkB is an inducible factor which is present in a wide variety of cell types. This factor regulates the transcription of a wide variety of cellular and viral genes including c-myc, the interleukins, receptors, adhesion molecules, p53 and the CMV early promoter. This factor is induced in response to a variety of primarily pathogenic stimuli including IL-1, TNF-$\alpha$, adhesion, bacterial lipopolysaccharides (LPS), and oxidative stress. Because induction of NFkB is blocked by antioxidants, it is believed that activation of NFkB employs reactive oxide intermediates (ROIs) as intracellular second messengers in response to the above stimuli.

Calpain inhibitor I has been shown to be an inhibitor of the proteolysis of IkB and hence of an inhibitor of the activation of NFkB. Ruetten and Thiemmermann (1997) Br. J. Pharmacol 121:695–704. Similar studies indicating that the subsequent degradation of IkB involves calpains and that calpain inhibitors decrease NFkB activity exist. For example, Milligan, et al. indicate that CI-1 decreases the nuclear translocation of NFkB and that CI-1 inhibited the degradation of IkB, Arch Biochem Biophys (1996) 335: 388–395. See also, Claudio, et al. (1996) Exp Cell Res 224:63–71 ("The activation of NFKB can be blocked by the cysteine protein inhibitor calpain inhibitor I"). Parry, et al. indicated that N-acetylleucinyl-leucinyl-norleucinal induced proteosome inhibition could block expression of a reporter gene under the control of the NFkB inducible MCP-1 promoter. Arterioscler Thromb Vasc Biol (1998) 18:934–940. However, calpain inhibition had no effect on expression of the MCP-1 driven reporter gene, stating "[t]he effects of [N-acetyl-leucinyl—leucinyl-norleucinal]were due to its inhibition of the proteasome in addition to calpain, because other calpain inhibitors had no effect on MCP-1 expression. In contrast to TPCK, which blocks NFkB translocation at the nucleus, [N-acetyl-leucinyl—leucinyl-norleucinal] had no effect on NFkB nuclear tranlocation or IL-1$\beta$ induced phosphorylation of p65."

Figure 10:
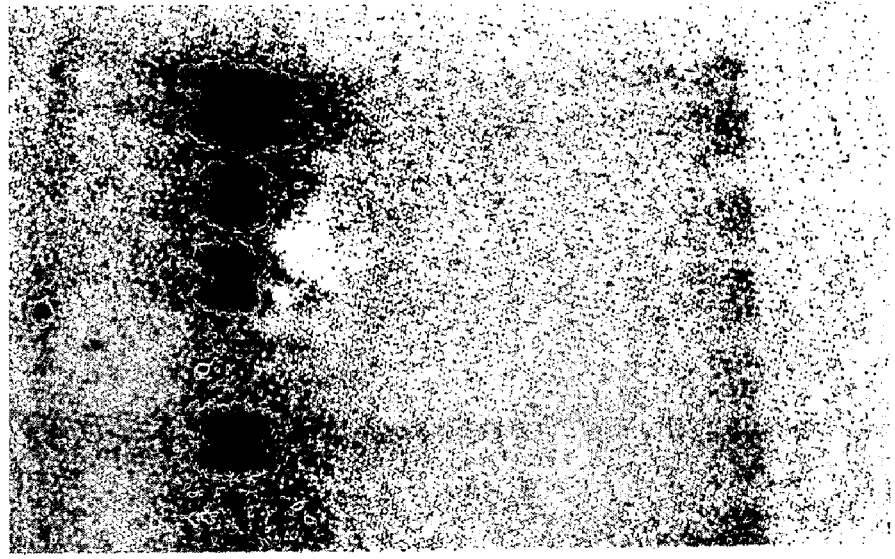
FIG. 10 presents the results of a gel shift assay demonstrating the activation of NF-kB and AP-1 in the HLF hepatocellular carcinoma cell line measured at 24 hours post treatment as more fully described in Example 8. The lanes on the gel are labelled as follows: Lane 1=DMF solvent alone control; Lane 2=10 µM CI-1; Lane 3=a null control vector based on ACN53 without the p53 transgene (ZZCB); Lane 4=ZZCB+10 µM CI-1; Lane 5=ACN53 alone and Lane 6=ACN53+ 10 µM CI-1. Panel A illustrates the induction of NF-kb upon administration of calpain inhibitor 1. Panel B illustrates the induction of AP-1 upon administration of calpain inhibitor 1.
Figure 10:
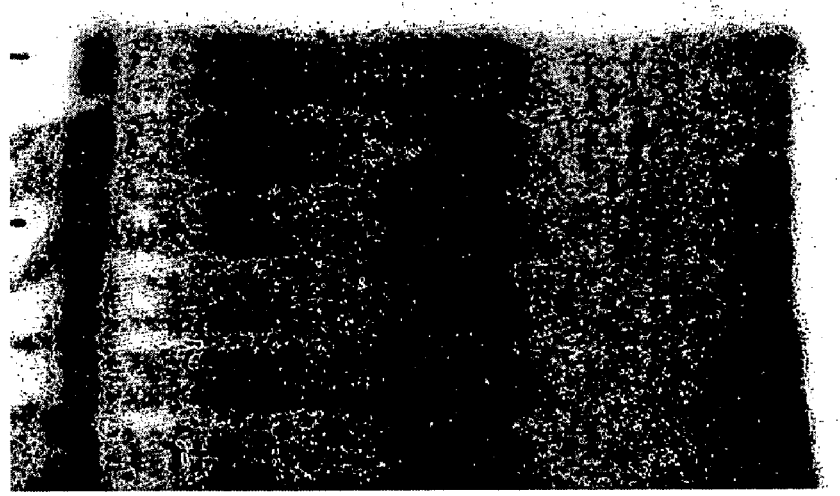
Figure 11:
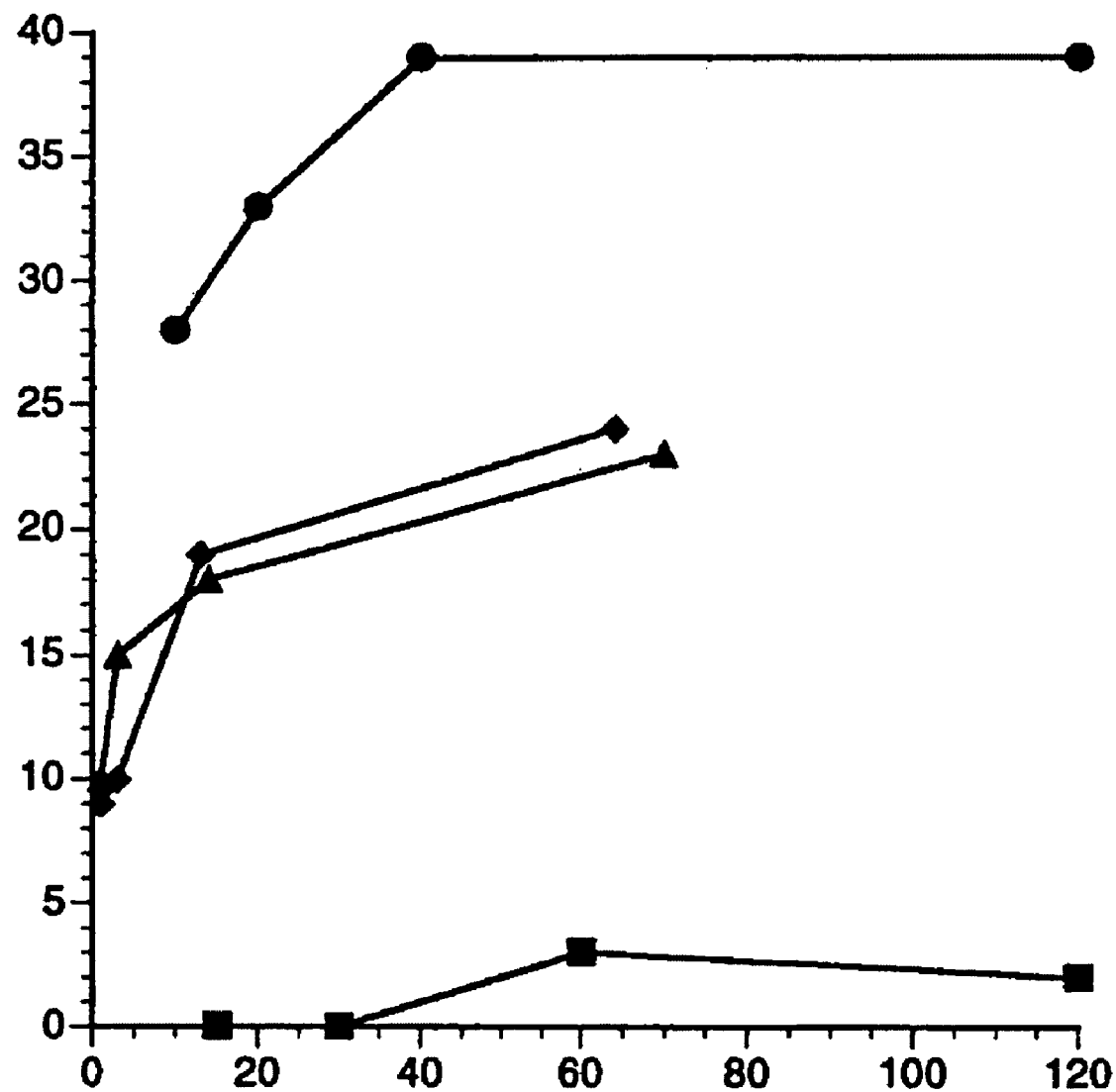
FIG. 11 is a graphical results of the cytotoxicity assay of CTL against ACN53 transduced EL-4 targets in C57/B16 mice injected with 60 mg/Kg (A) or 120 mg/Kg (♦) calpain inhibitor 1 in combination with ACN53 as more fully described in Example 7 herein. Percent lysis is plotted on the vertical axis and time on the horizontal axis. The ACN53 alone is represented by the circles (●) and the naive control level is represented by the squares (■). As can be seen from the data presented, the CTL response to ACN53 was substantially reduced in the presence of calpain inhibitor 1.

In contrast to these studies, the present invention further provides a method of enhancing transcription of a therapeutic transgene from the CMV promoter. The term "enhancing transcription" refers to an increase in the transcriptional activity of those sequences operably linked to the CMV promter. The term CMV promoter means the immediate early promoter of the cytomegalovirus. The promoter may be isolated as a restriction endonuclease fragment from the commercially available vector pCMVβ (GenBank Accession Number U02451). NFkB has been conclusively demonstrated to enhance transcription from the CMV promoter. The CMV promoter is a strong constituitive promoter widely utilized in the expression of exogenous transgenes from viral vectors. Recent reports indicated an upregulation of the CMV promoter driven genes in response to recombinant adenoviral infection. Loser, et al. (1998) J. Virol. 72:180–190. As previously indicated, the addition of agents which raise intracellular p53 concentration, regardless of mechanism, are desired to induce p53 mediated apoptosis. The ability of CI-1 to enhance NF-kb and AP-1 levels was demonstrated using a gel shift assay as more fully described in Example 8 below. The results are presented in FIG. 10 of the attached drawings. In response to calpain inhibitor 1 treatment, a 42% increase in NF-kB activation was detected, and a 50% increase in AP1 activation was detected as quantified by densitometer readings. The results of the gel shift assay demonstrate the ability of CI-1 to enhance the levels of NF-KB and AP-1 in the HLF hepatocellular carcinoma cell line. While not being limited by any mechanism of action, the use of CI-1 demonstrably increases the level of p53 produced by ACN53 in a cell may involve upregulation of the p53 transgene driven by the CMV promoter by the in vivo stabilization of NFkB. Also, the transcriptional factor AP1 is activated in response to calpain inhibitor 1 treatment, and there are AP1 binding sites on the CMV promoter for activation of promoter.

These results were confirmed in vivo. Two C57BL/6 mice were treated with 60 mg/kg injected intraperitoneally on day minus one. Three control mice were injected with CI-1 solvent only (PBS/0.02% DMSO). On day zero, all mice were tail vein injected with $9\times10^9$ particle/ml with a recombinant adenovirus encoding the beta-galactosidase transgene. CI-1 or solvent was administed one additional time on day one for three total intraperitoneal administrations of CI-1. Mice were sacrificed three days and nine days later (four-and ten days post-infection respectively), and livers were harvested for quantitative PCR and RT-PCR to detect viral DNA and viral transcript (b-galactosidase) respectively. One third of the miceexpressed a high level of transgene RNA in response to calpain inhibitor 1 treatment, as compared with virus alone. Approximately a six fold higher level was observed.

E. Use of Calpain Inhibitors to Decrease the In Vivo CTL Response to Recombinant Adenoviral Vectors The present invention also provides a method to suppress the in vivo CTL response to viral vectors by the use of calpain inhibitors. N-acetyl-leucinyl—leucinyl-norleucinal (Calpain Inhibitor I) has proteosome as well as calpain inhibitor activity. At concentrations below 50 $\mu$M, CI-1 is primarily an inhibitor of calpain. However, above 50 $\mu$M, CI-1 has been shown to inhibit proteasome function. This inhibition effects antigenic peptide presentation to T cells as the proteosome is the primary enzymatic complex that degrades proteins into peptides prior to insertion into the ER through the TAP complex where loading onto MHC class I occurs (Rock, et al.). Thus class I restricted responses by T cells are inhibited due to the lack of sufficient class I MHC peptide complexes; the ligand for T cell receptors on CD8+ T cells. The calpain inhibitors may also effect antigen presentation by a mechanism that is not generally obvious. Namely, the calpain inhibitor may inhibit apoptosis of non-transduced cells such as antigen presenting cells (e.g., macrophages, dendritic cells) which may affect the capacity for antigen transfer to dendritic cells through phagocytosis of the apoptotic cells, thus effecting maturation of the dendritic cells and antigen presentation function following migration to regional lymphnodes where the dendritic cells activate T cells.

Figure 8:
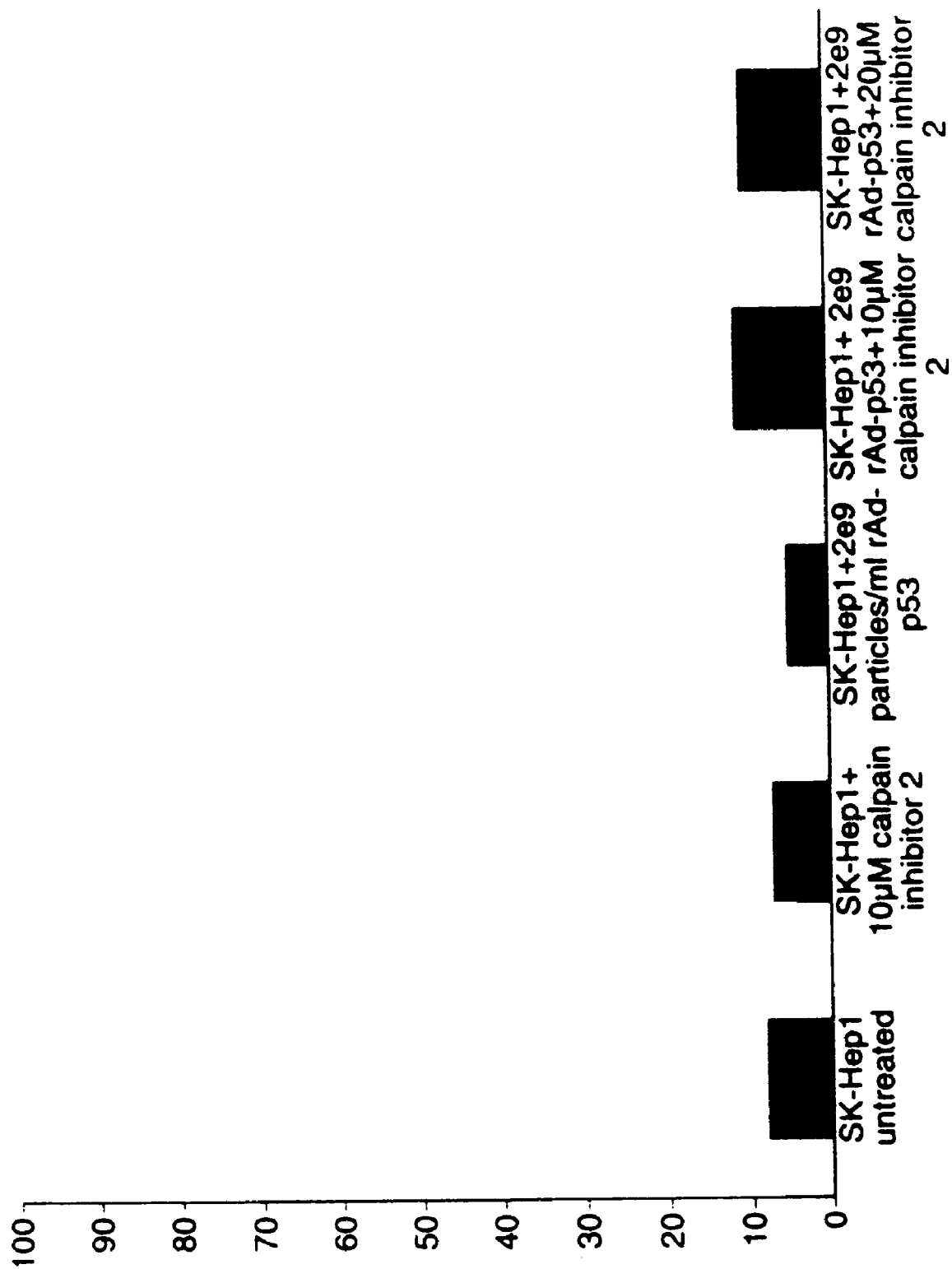
FIG. 8 is a graphical representation of the data obtained by the administration of calpain inhibitor 2 in combination with a recombinant adenvirus encoding p53 to the SK-Hep-1 hepatocellular carcinoma cell line. The cells were treated with the combinations indicated below each histogram and measured for apoptosis by annexin V staining at 17 hours post treatment. The percentage of cells positive for annexin V staining is indicated on the vertical axis. As can be seen from the data presented in combination with the data presented earlier, the induction of apoptosis is selective to inhibitors of microcalpains.
Figure 9:
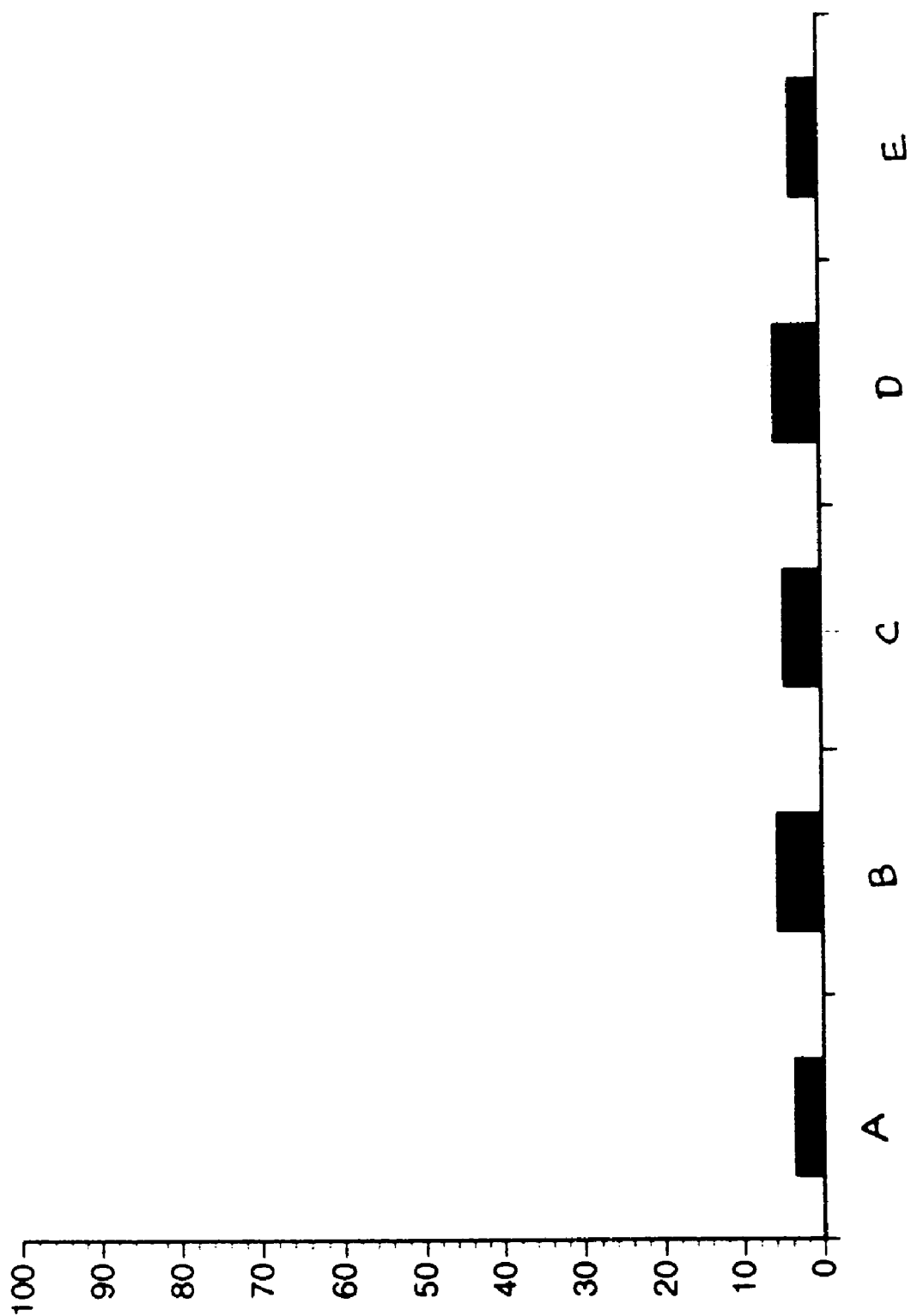
FIG. 9 is a graphical representation of the data obtained by the administration of calpain inhibitor 1 in combination with a recombinant adenovirus encoding p53 to primary ocular fibroblast cells. The cells were treated as follows: A=untreated control cells; B=treatment with 10 µM CI-1 alone; C=$1\times10^9$ particles of ACN53 alone; D=10 µM CI-1 in combination with $1\times10^9$ particles of ACN53; E=20 µM CI-1 in combination with $1\times10^9$ particles of ACN53 indicated below each histogram and measured for apoptosis by annexin V staining at 26 hours post treatment. The percentage of cells positive for annexin V staining is indicated on the vertical axis. As can be seen from the data presented, calpain inhibitor 1 incombination of ACN53 failed to induce apoptosis in primary ocular fibroblasts.

The applicants hypothesized that the combined effect on MHC Class 1 presentation and apoptosis of non-transduced will reduce the immune response to the viral vectors. This was confirmed in a in vivo mouse model in substantial accordance with the teaching of example & herein. The results are shown in the FIG. 8 of the attached drawings. The results show that intravenous administration of $9\times10^9$ PN/mouse elicited a vigorous CTL response as compared to naive animals administered only buffer. Moreover the data show that treatment with the calpain inhibitor at two different concentrations resulted in a significant inhibition of the CTL response in BGCG injected mice. There was greater than a five-fold decrease in the relative number of CTL lytic-units upon treatment with calpain inhibitor CI-1 as determined by measuring the relative effector to target ratio which results in 25% killing. This data demonstrates that the effects of the CI-1 treatment on the immune response further augments the relative capacity to administer p53 gene therapy by transiently inhibiting the immune response to the adenovirus vector treatment.

F. Pharmaceutical Formulations:

The present invention further provides a pharmaceutical formulations of p53 and a calpain inhibitor in a pharmaceutically acceptable carrier.

The term "formulation" refers to pharmaceutical formulations comprising a protein, viral or non-viral delivery system for administration in vivo or ex vivo to an individual in need of treatment. In vivo administration will typically employ the compositions of the present invention formulated for intramuscular, intravenous, intrarumoral, intrahepatic artery, intraperitoneal or intrvesicular, injectable depot-type devices or topical routes of administration. Examples wherein the compositions of the present invention include polymer matrices, hydrogel matrices, polymer implants, or encapsulated formulations to allow slow or sustained release of the compositions. Examples of formulations for the delivery of transgenes via non-viral delivery systems to the airway epithelia is described in Debs and Zhu, U.S. Pat. No. 5,641,622 issued Jun. 24, 1997.

Again, p53 refers to the p53 protein therapy and gene therapy systems for the delivery of a nucleotide sequence encoding p53. While the combined effect of p53 and the calpain inhibitor are not limited to a given vehicle for the introduction of the p53 molecule, in the preferred practice of the invention, the p53 molecule is introduced by gene therapy methods using a viral vector derived from genus adenoviridiae. Particularly preferred viruses are derived from the human adenovirus type 2 or type 5. Such viruses are preferably replication deficient by modifications or deletions in the E1a and/or E1b coding regions. Other modifications to the viral genome to achieve particular expression characteristics or permit repeat administration or lower immune response are preferred. More preferred are recombinant adenoviruses having complete or partial deletions of the E4 coding region, optionally retaining E4orf6 and E4orf6/7. The E3 coding sequence may be deleted but is preferably retained. In particular, it is preferred that the promoter operator region of E3 be modified to increase expression of E3 to achieve a more favorable immunological profile for the therapeutic vectors. Most preferred are human adenoviral type 5 vectors containing a DNA sequence encoding p53 under control of the cytomegalovirus promoter region and the tripartite leader sequence having E3 under control of the CMV promoter and deletion of E4 coding regions while retaining E4orf6 and E4orf6/7. In the most preferred practice of the invention as exemplified herein, the vector is ACN53, as described in Wills, et al. (1994) Human gene therapy 5:1079–1088.

The term "carriers" refers to compounds commonly used on the formulation of pharmaceutical compounds used to enhance stability, sterility and deliverability of the therapeutic compound. When the viral, non-viral or protein delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The terms "delivery enhancers" or "delivery enhancing agents" are used interchangeably herein and includes agents which facilitate the transfer of the nucleic acid or protein molecule to the target cell. Examples of such delivery enhancing agents detergents, alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol. Acetates such as acetic acid, gluconic acid, and sodium acetate are further examples of delivery-enhancing agents. Hypertonic salt solutions like 1M NaCl are also examples of delivery-enhancing agents. Examples of surfactants are sodium dodecyl sulfate (SDS) and lysolecithin, polysorbate 80, nonylphenoxypolyoxyethylene, lysophosphatidylcholine, polyethylenglycol 400, polysorbate 80, polyoxyethylene ethers, polyglycol ether surfactants and DMSO. Bile salts such as taurocholate, sodium tauro-deoxycholate, deoxycholate, chenodesoxycholate, glycocholic acid, glycochenodeoxycholic acid and other astringents such as silver nitrate may be used. Heparin-antagonists like quaternary amines such as protamine sulfate may also be used. Cyclooxygenase inhibitors such as sodium salicylate, salicylic acid, and non-steroidal antiinflammatory drug (NSAIDS) like indomethacin, naproxen, diclofenac may be used. Delivery-enhancing agents includes compounds of the formula I:

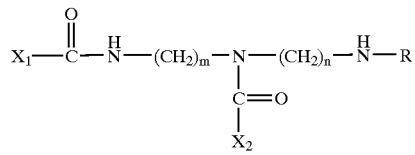

wherein X1 and X2 are selected from the group consisting of a cholic acid group, a deoxcholic acid group and a saccharide group, m is an integer from 2 to 8 and preferably 2 or 3, n is an integer from 2 to 8 and preferably 2 or 3, and R is a cationic group, a saccharide group or a structure —CO—X3 wherein X3 is a sachharide group. The saccharide group may be selected from the group consisting of pentose monosaccharide groups, hexose monosaccharide groups, pentose—pentose disaccharide groups, hexose—hexose disaccharide groups, pentose-hexose disaccharide groups, and hexose-pentose disaccharide groups.

The term "detergent" includes anionic, cationic, zwitterionic, and nonionic detergents. Exemplary detergents include but are not limited to taurocholate, deoxycholate, taurodeoxycholate, cetylpyridium, benalkonium chloride, Zwittergent®3–14 detergent, CHAPS (3-[(3-Cholamidopropyl) dimethylammoniol]-1-propanesulfonate hydrate), Big CHAP, Deoxy Big CHAP, Triton®-X-100 detergent, C12E8, Octyl-B-D-Glucopyranoside, PLURONIC®-F68 detergent, Tween® 20 detergent, and TWEEN® 80 detergent (CalBiochem®_Biochemicals).

The pharmaceutical formulation may be provided in a single premixed formulation or provided in a kit of parts for mixing by the end user. The term "kit" as used herein refers to a unit packaged combination of the elements of a formulated calpain inhibitor and a protein, viral or non-viral p53 formulation. Such kits promote the proper use and formulation of the materials when used in combination and avoid improper dosing. The formulated elements of the kit may be in ready to use or precursor form (e.g. lyophilized form) requiring reconsitution in a solution. The kit preferably contains the appropriate carriers and solvents to reconstitute the precursor form of the p53 and calpain inhibitor elements.

G. Methods of Use:

The present invention provides a method of ablating neoplastic cells in a mammalian organism in vivo by the co-administration of a calpain inhibitor and p53.

The term "ablating" means the substantial reduction of the population of viable neoplastic cells so as to alleviate the physiological maladictions of the presence of the neoplastic cells. The term "substantial" means a reduction in the population of viable neoplastic cells in the mammalian organism by greater than approximately 20% of the pre-treatment population. The term "viable" means having the uncontrolled growth and cell cycle regulatory characteristics of a neoplastic cell. The term "viable neoplastic cell" is used hereing to distinguish said cells from neoplastic cells which are no longer capable of replication. For example, a tumor mass may remain following treatment, however the population of cells comprising the tumor mass may be dead. These dead cells have been ablated and lack the ability to replicate, even though some tumor mass may remain.

The term "neoplastic cell" is a cell displaying an aberrant growth phenotype characterized by independence of normal cellular growth controls. As neoplastic cells are not necessarily replicating at any given time point, the term neoplastic cells comprise cells which may be actively replicating or in a temporary non-replicative resting state (G1 or G0). Localized populations of neoplastic cells are referred to as neoplasms. Neoplasms may be malignant or benign. Malignant neoplasms are also referred to as cancers. The term cancer is used interchangeably herein with the term tumor. Neoplastic transformation refers the conversion of a normal cell into a neoplastic cell, often a tumor cell.

The term "mammalian organism" includes, but is not limited to, humans, pigs, horses, cattle, dogs, cats. The methods and compositions of the present invention may be used for the treatment of a variety of organisms suffering from of diseases associated with p53 dysfunction and may be used to eliminate p53 negative cells from a population of cells. For example, the formulations and methods of the present invention may be used for the treatment of a variety of mammalian species suffering from such maladies including humans, pigs, horses, cattle, dogs, cats, preferably by employing vectors encoding, for example, human p53, porcine p53, equine p53, bovine p53, canine p53 (Velhoen & Milner (1998) Oncogene 16:1077–1084), feline p53, etc. respectively. Preferably one employs an adenoviral vector endogenous to the mammalian type being treated. Although it is generally favored to employ a virus from the species to be treated, in some instances it may be advantageous to use vectors derived from different species which possess favorable pathogenic features. For example, it is reported (WO 97/06826 published Apr. 10, 1997) that ovine adenoviral vectors may be used in human gene therapy to minimize the immune response characteristic of human adenoviral vectors. By minimizing the immune response, rapid systemic clearance of the vector is avoided resulting in a greater duration of action of the vector.

The term "co-administration" refers to the administration within a sufficient time such that the therapeutic effect of one element has not been eliminated prior to the administration of the second agent. For example, it has been observed that the prior treatment of cells with calpain inhibitor 1 will increase the infectivity of those cells to viral vectors. Consequently, although not administered at the same time, the calpain inhibitor is deemed to be co-administered with the virus when the infectivity enhancing effect of the calpain inhibitor persists.

Examples of diseases currently demonstrated as candidates for treatment with p53 therapy include a broad variety of cancers commonly associated with p53 mutations. Approximately 65% of all cancer cell types studied to date implicate that p53 dysfunction is associated with the neoplastic phenotype of these cells. Consequently, these cancers are the primary cancers such as ovarian cancer, head and neck cancer, Based on the foregoing data presented herein, in a given application, one would expect that the dosage of a recombinant adenoviral vector encoding p53 may be decreased by approximately a factor of 2 logs when the concentration of CI-1 is approximately 10 $\mu$M $\mu$M to achieve intracellular p53 dosage substantially equivalent to the administration of the rAd-p53 vector alone. The total dosage of the p53 to be administered to an organism in need of treatment is based on a variety of factors. When viral vector delivery systems are employed in p53 gene therapy such factors include the infectivity of the particular vector with respect to the target cell, the total number of viral copies of the virus produced in the target cell, the relative strength of the control regions used to express the p53 molecule (i.e the intracellular and particularly intranuclear p53 concentration), etc. In the case of p53 protein therapy (as well as p53 gene therapy) one must also consider the effects of diffusion/dissolution, the nature of the route of administration (e.g., localized versus systemic), the particular activity of the p53 species employed. However, these factors may be readily determined by those of skill in the art. For example, in the case of the recombinant viral vector ACN53, the optimal human dose of has been determined in human clinical trials to be approximately $2\times10^{13}$ PN. Consequently, one may readily determine based on the above data that a substantially equivalent effective dose of ACN53 may be decreased by a factor of 2 log in combination with a 10 $\mu$M concentration of CI-1. The formulations of the present invention also provide a means to increase p53 dose or increase p53 expression without the need to increase the vector dose which is associated with toxicity in some systems.

The method of the present invention may be employed in combination with conventional chemotherapeutic agents or treatment regimens. Examples of such chemotherapeutic agents include inhibitors of purine synthesis (e.g., pentostatin, 6-mercaptopurine, 6-thioguanine, methotrexate) or pyrimidine synthesis (e.g. Pala, azarbine), the conversion of ribonucleotides to deoxyribonucleotides (e.g. hydroxyurea), inhibitors of dTMP synthesis (5-fluorouracil), DNA damaging agents (e.g. radiation, bleomycines, etoposide, teniposide, dactinomycine, daunorubicin, doxorubicin, mitoxantrone, alkylating agents, mitomycin, cisplatin, procarbazine) as well as inhibitors of microtubule function (e.g vinca alkaloids and colchicine). Chemotherapeutic treatment regimens refers primarily to non-chemical procedures designed to ablate neoplastic cells such as radiation therapy. Examples of combination therapy when the therapeutic gene is p53 are described in Nielsen, et al. WO/9835554A2 published Aug. 20, 1998. Examples of the utility of the combination of p53 and DNA damaging compounds are described in U.S. Pat. No. 5,747,469 issued May 5, 1998.

The immunological response is significant to repeated in vivo administration of viral vectors. Consequently, the method of the present invention may include the co-administration of immunosuppressive agents. Examples of immunosuppressive agents include cyclosporine, azathioprine, methotrexate, cyclophosphamide, lymphocyte immune globulin, antibodies against the CD3 complex, adrenocorticosteroids, sulfasalzaine, FK-506, methoxsalen, and thalidomide. Alternatively, when selectively replication or conditionally replication adenoviral vectors are employed, the elimination of E3-11.6K protein to minimize cell lysis induced by adenovirus until apoptosis is achieved. This would minimize the immune response until after the initial round of localized spreading occurs. At this later time, once apotosis of the initially infected cells is achieved and localized virus spreading is permitted, the immune response would be advantageous.

The present invention also provides a method of ablating neoplastic cells in a population of normal cells contaminated by said neoplastic cells ex vivo by the administration of a recombinant adenovirus of the present invention to said population. An example of the application of such a method is currently employed in ex vivo applications such as the purging of autologous stem cell products commonly known as bone marrow purging. The term "stem cell product" refers to a population of hematopoietic, progenitor and stem cells capable o reconstitutin gthe long term hematpoietic function of a patient who has received myoablative therpay. Stem cell products are conventionally obtained by apheresis or mobilized or non-mobilized peripheral blood. Apheresis is conventionally achieved through the use of known procedures using commercially available apheresis apparatus such as the COBE Spectra Apheresis System, commercially available from COBE International, 1185 Oak Street, Lakewood, Colo. It is preferred that treatment conditions be optimized to achieve a "3-log purge" (i.e. removal of approximately 99.9% of the tumor cells from the stem cell produce) and most preferably a "5-log purge" (removal of approximately 99.999% of tumor cells from the stem cell product). In the preferred practice of the invention, a stem cell product of 100 ml volume would be treated with up to $5\times10^{11}$ particles per milliter ($5\times10^{13}$ particles) of the recombinant adenovirus of the present invention for a period of approximately 4 hours at 37C. P53 gene therapy, particularly the use of adenoviral vectors encoding p53 have been used to effectively purge tumor cells from a population of stem cells. Results to date indicate that approximately $8\times10^9$ PN/ml of stem cell product achieve the 5-log purge considered optimal for autologous implantation. As indicated from the data presented, the use of calpain inhibitors can enhance the effect of rAd-p53 vectors by reducing the dosage by approximately 2 logs. Additionally, the data presented indicates that treatment of the cells with CI-1 increases the infectivity of the cells to rAd vectors by an additional 1–3 logs depending on the timing of the calpain inhibitor treatment. Thus, the combination of pretreatment with CI-1 in combination with a rAd-53 gene therapy would be expected to reduce the dosage required to achieve a 5-log purge by approximately 3–4 logs. Thus an effective dose of ACN53 for a 5 log purge of a stem cell product would be approximately $1\times10^7$ to approximately $5\times10^8$ PN/ml in the presence of 10 $\mu$M CI-1.

EXAMPLES

The following examples provide the methodology and results of experiments demonstrating the recombinant adenoviruses expressing the p53. It will be apparent to those of skill in the art to which the invention pertains, the present invention may be embodied in forms other than those specifically disclosed above, without departing from the spirit or essential characteristics of the invention. The particular embodiments of the invention described below, are therefore to be considered as illustrative and not restrictive. In the following examples, "g" means grams, "ml" means milliliters, "mol" means moles, "° C." means degrees Centigrade, "min." means minutes, "FBS" means fetal bovine serum, and "PN" specifies particle number.

Example 1

Construction of Viral Vectors

A viral vector backbone was created based on a human adenovirus type 5 genome comprising deletions of the E1a and E1b and protein IX gene functions and partial deletion of the E3 coding region. Specifically, the deletions of base pairs 355 to 3325 was used to eliminate E1a and E1b functions, deletion of base pairs 3325 to 4021 was used to eliminate protein IX function and deletions of 28592 to 30470 were used to eliminate E3 functions. See Wills, et al. (1994) Human Gene Therapy 5:1079–1088. The DNA sequence encoding the cytomegalovirus immediate early promoter without the presence of the CMV promoter intron was inserted into the rAd viral genome. This vector without an exogenouse transgene was used as control vector and was designated ZZCB. The wildtype p53 coding sequence was inserted into this vector backbone so as to achieve expression of the p53 sequence under control of the CMV promoter. This vector was denoted ACN53 and is also referred to interchangeably as FTCB.

Example 2

Culture of Tumor Cell Lines

Hep 3B 2.1–7 cells were obtained from the American Type Culture Collection, Peoria, Ill. under accession number ATCC # HB 8064). NCI-H596 cells were obtained from the American Type Culture Collection, Peoria, Ill. under accession number ATCC # HTB 178). NCI—H596 cells were grown in Ham's F-12 DMEM (commercially available from Irvine Scientific) supplemented with sodium pyruvate and 10% fetal bovine serum. HLF cells were obtained from the Japanese Cancer Research Resource Bank, National Institute of Health, Tokyo, Japan). SK-Hep1 cells were obtained from the American Type Culture Collection, Peoria, Ill. under accession number ATCC #HTB 52). RKO cells were obtained from M. Brattain, Medical College Hospital, Toledo, Ohio. DLD-1 cells were obtained from the American Type Culture Collection, Peoria, Ill. under accession number ATCC # CCL 221). Hep 3B 2.1–7 cells were obtained from the American Type Culture Collection, Peoria, Ill. under accession number ATCC # BB 8064). NCI-H596 cells were obtained from the American Type Culture Collection, Peoria, Ill. under accession number ATCC # HTB 178). All cell lines with the exception of NCI-H596 were grown in Delbecco's Modified Eagles media (DME) supplemented with sodium pyruvate and 10% fetal bovine serum. NCI-H596 cells were grown in Ham's F-12 DME supplemented with glutamine and 10% fetal bovine serum.

Example 3

Apoptotic Effect Of Virus and/or CI-1 on Tumor Cells

An aliquot containing approximately $1\times10^6$ cells of each type was placed in a T-225 flask. The effect of varying concentrations of rAd-p53 (from $1\times10^7$ to $2\times10^9$ACN53 particles/ml of solution) was investigated in combination with CI-1 in a range of 5–20 $\mu$M. In each instance, the cell line was infected with $1\times10^7$–$1\times10^9$ particles/ml of cell culture with the ACN53 using the empty cassette virus (ZZCB) as a control. In each instance, the cells were exposed to the virus for a period of one hour. At the end of this time, the virus was washed off the from the cells and fresh media containing an appropriate concentration of CI-1 was added.

HLF cells were infected at increasing log concentrations of rAd-p53 ranging from $1\times10^5$ to $1\times10^9$ for one hour at which time virus was washed off and replaced with fresh media (viral infection with no treatment) or with 10 $\mu$M calpain inhibitor 1. Cells were assayed for apoptosis by annexin V-FITC staining at 24 and 42 hours post-infection.

CI-1 was obtained from Boehringer-Mannheim Biochemicals (Indianapolis, Ind.). The CI-1 containing media was prepared as follows. CI-1 was diluted in dimethylformamide (DMF) to a concentration of 33.3 $\mu$M/$\mu$l. The CI-1 solution in DMF was added to achieve a final concentration in the media of 5 or 10 $\mu$M final concentration of CI-1. An equivalent volume of DMF alone was added to the control cells. Calpain inhibitor 2, N-acetyl-leu—leu-methioninal (Boehringer Mannheim) was added to cell lines at 5–50 $\mu$M final concentration with or without rAd-p53 for 26 hours.

At a time of 17 (or 26 hours) post infection, the percentage of cells undergoing apoptosis was determined by convential apoptotic markers. Apoptosis was monitored visually by observing blebbed nuclei characteristic of apoptosis, by propidium iodide staining (using propidium iodide commercially available from Molecular Probes, Inc.) followed by flow cytometric analysis to look for subgenomic populations of cells, and by labeling cells with annexin V-FITC (commercially available from Boehringer Mannheim) in substantial accordance with the instructions provided by the manufacturer, followed by flow cytometric analysis on a FACScan Flow Cytometer (commercially available from Becton Dickinson).

Figure 3:
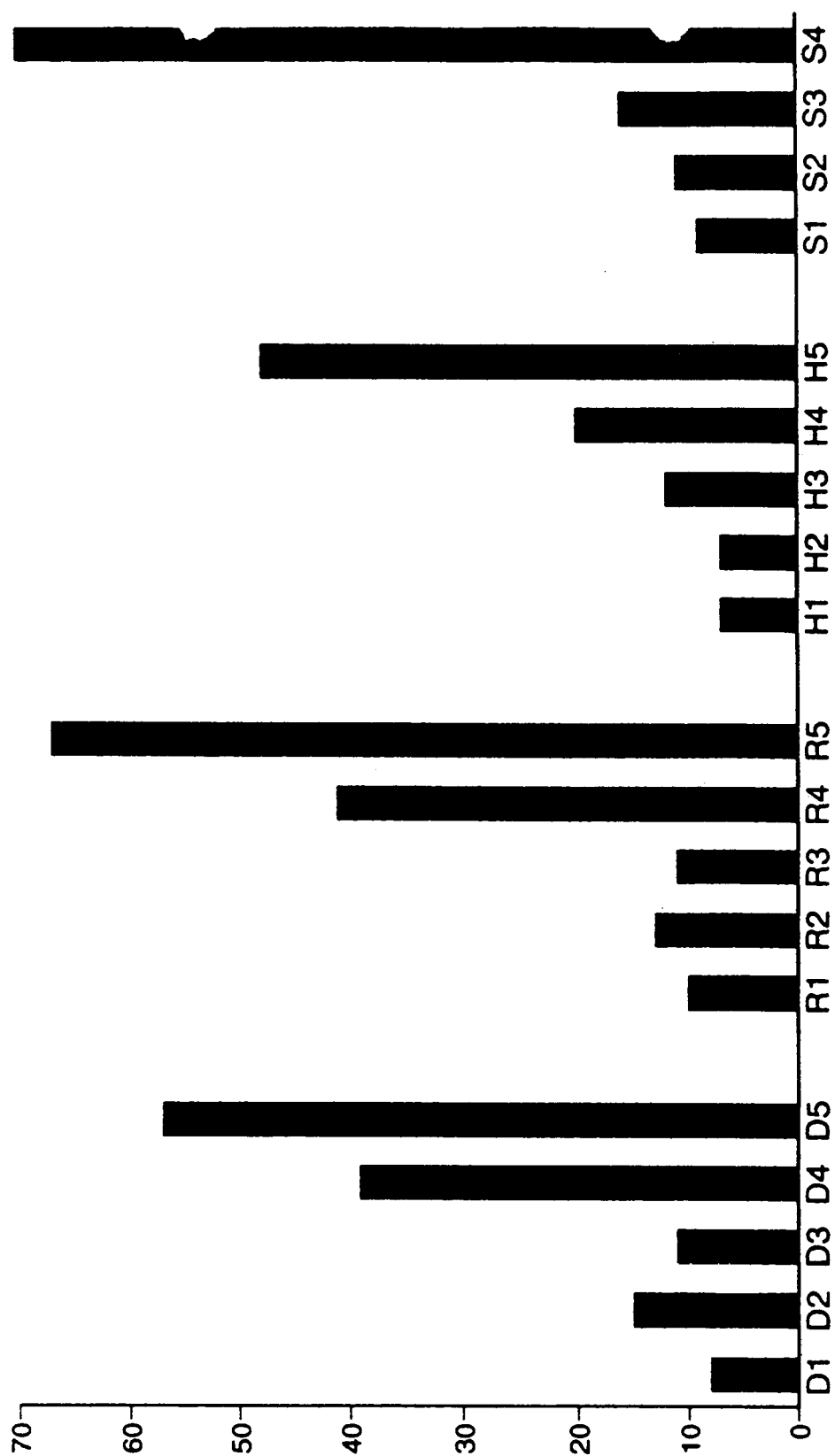
FIG. 3 is a histogram representing the percentage of cells undergoing apoptosis (vertical axis) measured at 17 hours post treatment in response to the adminstration of various concentrations of rAd-p53 and/or CI-1. Histogram D1=untreated DLD1 cells, histogram D2=DLD1 cells in response to 10 $\mu$M CI-1; histogram D3=DLD1 cells in response to 1×10$^9$ rAd-p53; histogram D4 DLD1 cells in response to 5 $\mu$M CI-1 plus 1×10$^9$ rAd-p53; histogram D5=DLD1 cells in response to 10 $\mu$M CI-1 plus 1×10$^9$ rAd-p53; histogram R1=untreated RKO cells, histogram R2=RKO cells in response to 20 $\mu$M CI-1; histogram R3=RKO cells in response to 1×10$^9$ rAd-p53; histogram R4=RKO cells in response to 10 $\mu$M CI-1 plus 1×10$^9$ rAd-p53; histogram R5=RKO cells in response to 20 $\mu$M CI-1 plus 1×10$^9$ rAd-p53. cells; histogram H1=untreated HLF cells, histogram H2=HLF cells in response to 10 $\mu$M CI-1; histogram H3=HLF cells in response to 1×10$^9$ rAd-p53; histogram H4=HLF cells in response to 5 $\mu$M CI-1 plus 1×10$^9$ rAd-p53; histogram H5=HLF cells in response to 10 $\mu$M CI-1 plus 1×10$^9$ rAd-p53; histogram S1=untreated SK-Hep1 cells, histogram S2=SK-Hep1 cells in response to 5 $\mu$M CI-1; histogram S3=SK-Hep1 cells in response to 2×10$^9$ rAd-p53; histogram S4=SK-Hep1 cells in response to 5 $\mu$M CI-1 plus 2×10$^9$ rAd-p53.

The results of these experiments are presented in FIGS. 1 and 3 of the attached drawings and Tables 2 and 3 above. As can be seen from the data presented, the combination of ACN53 and CI-1 markedly increased the percentage of cells undergoing apoptosis in comparison with the administration of either agent alone and in comparison with control virus.

Example 4

Determination of G0/G1 Phase Cell Cycle Arrest by Treatment with CI-1

In order to determine any increases in p53 function in response to calpain inhibitor 1, the quantity of cells undergoing G0/G1 cell cycle arrest in response to CI-1 administration, was assayed by bromodeoxyuridine labeling of cells. Each of the cell lines described in Example 2 above were exposed to a concentration of 0 or 5 $\mu$M CI-1 (in DMF) as described in Example 3 above. Cell lines treated with DMF alone or 5 $\mu$M final concentration of calpain inhibitor 1 for 17 hours were pulse labeled with a final concentration of 10 $\mu$M bromodeoxyuridine (Boehringer Mannheim) for two hours. Cells were harvested for bivariate BrdU/DNA flow cytometric analysis by fixation in 70% ethanol, followed digestion with 0.08% pepsin for 30 minutes at 37 degrees. Cells were centrifuged at 1500 RPM, and 2N HCL was added. Cells were incubated at 37 degrees for 20 minutes, followed by addition of 1M sodium borate. Cells were washed in IFA/tween 20 (0.01 M HEPES, 0.005% sodium azide, 0.5% tween 20, 5% FBS, 3.75M NaCl), and anti-BrdU antibody, diluted 1:10 in IFA without tween 20, was added for 30 minutes. Cells were washed in IFA/tween 20, and incubated in IFA/tween 20/RNase for 15 minutes at 37 degrees.

Cells that had incorporated BrdU were stained using a FITC conjugated monoclonal antibody to BrdU (commercially available from Becton-Dickinson) and detected by FACS analysis on a FACScan FACS machine (commercially available from Becton Dickinson).

Example 5

Western Blotting

At 17 hours post treatment, cells were lysed in protein lysis buffer (50 mM tris, 250 mM NaCl, 50 mM NaF, 5 mM EDTA and 0.1% NP-40 with 1 mM PMSF). Cell lysates were subjected to electrophoresis. 10 $\mu$g of protein was added per lane on a 12% polyacrylamide gel and transfered onto nitrocellulose membranes. The membranes were subjected to western blot analysis using antibodies specific for p53 or p21 (Calbiochem, p53 antibody Ab-6, and p21 antibody Ab-7). HRP-conjugated secondary antibody (Amersham) was added for one hour at which time the blots were washed. Blots were developed using enhanced chemiluminescence detection system (Amersham) and quantitated using NIH imaging analysis.

Example 6

PCR and RT/PCR

A. Quantitative PCR Assay:

Taqman® EZ RT-PCR core reagents (rTth DNA polymerase, AmpErase UNG, deoxy ATP, deoxy CTP, dexoy GTP, deoxy UTP, 5× Taqman® EZ buffer, and manganese acetate solution) were obtained from Perkin-Elmer, as Part No. N808-0236. Oligonucleotide Primer "A" "(5' Taqman® p53 5'-AACGGTACTCCGCCACC; SEQ ID NO:2) and Primer "B" (3' Taqman® p53; 5'-CGTGTCACCGTCGT GGA; SEQ ID NO:3) and 10 $\mu$M Taqman® Probe (5'-FAM-CAGCTGCTCGAGAGGTTTTCCGATCC-TAMRA; SEQ ID NO:4) were obtained from Perkin Elmer. Diethyl pyrocarbonate (DEPC) treated water was obtained from United States Biochemical Cat. No. 70783 or equivalent.). tRNA was obtained from Sigma Cat. No. R5636, 10 $\mu$g/ml.

A quantity of reverse transcription master mix (RT Master Mix) was prepared proportional to the number of samples to be amplififed. RT Master Mix for one sample comprises: 7 $\mu$L Mn(OAC)$_2$, 10 $\mu$L Gene Amp 5× Taqman® Buffer, 3 $\mu$L Oligonucleotide Primer "A", 10 $\mu$m, 3 $\mu$L Oligonucleotide Primer "B", 10 $\mu$m, 6 $\mu$L deoxynucleotide driphosphates, 0.5 $\mu$L of rTth polymerase, 0.5 $\mu$L UNG, and 1.5 $\mu$L Taqman® Probe, 10 $\mu$m and Q.S. to 49 $\mu$L with diethyl pyrocarbonate (DEPC) treated water.

Add 49 $\mu$L of the RT Master Mix to each tube (Perkin Elmer, Part No. N801-0933) and add 1 $\mu$L of sample or cRNA standard (see attachments) or RNase free water to each tube. Cap (Perkin Elmer, Part No. N801-0935) tubes and centrifuge at 600 rpm for 2 minutes. Transfer all the tubes to the thermocycler. Program the thermocycler (Perkin Elmer ABI Prism 7700 Sequence Detector) to use the following conditions in sequence:

50° C. for 2 minutes.
60° C. for 30 minutes.
95° C. for 10 minutes.
Denaturation step 95° C. for 15 seconds.
Annealing step 61° C. for 1 minute.

Repeat steps for an additional 39 cycles. The total number of cycles is 40.

B. PCR ASSAY

The following materials were obtained from Perkin Elmer Corporation under Part No. N808-0028: Gene Amp 10× Taqman Buffer A, 25 mM MgCl$_2$, 5 $\mu$M Oligonucleotide Primer "A", 5 $\mu$M Oligonucleotide Primer "B", 5 units/mL AmpliTaq® Gold DNA Polymerase, 10 $\mu$M Taqman Probe. Deoxynucleotide Triphosphates, dATP, dCTP, and dGTP are 10 mM. dUTP is 20 mM. Equal volumes of dNTPs were combined to give a concentration of 2.5 mM for dATP, dCTP, and dGTP and a concentration of 5 mM for dUTP. (Perkin Elmer Part No. N808-0095) and 1 unit/$\mu$L Uracil-N-glycosylase (UNG) (Perkin Elmer, Part No. N808-0096). Diethyl Pyrocarbonate (DEPC) treated water was obtained from United States Biochemical (Cat. No. 70783. The following primers and probe were used p53 PCR Primer "A" (5' Taqman p53) from 5'-3' is AAC GGT ACT CCG CCA CC (SEQ ID NO:2); Primer "B" (3' Taqman p53) from 5'-3' CGT GTC ACC GTC GTG GA (SEQ ID NO:3); Taqman probe (p53 Taqman Probe) from 5'-3' is FAM-CAG CTG CTC GAG AGG TTT TCC GAT CC-TAMRA (SEQ ID NO:4). The following primers and probe were used for B-Actin PCR.; Sequence of Primer "A" (5' Taqman B-Actin) from 5'-3' is TCA CCC ACA CTG TGC CCA TCT ACG A (SEQ ID NO:5); Primer "B" (3' Taqman B-Actin) from 5'-3' is CAG CGG AAC CGC TCA TTG CCA ATG G (SEQ ID NO:6); Taqman probe (B-Actin Taqman Probe) from 5'-3' is FAM-ATG CCC CCC CCA TGC CAT CCT GCG T-TAMRA (SEQ ID NO:7).

An amount of Master Mix (described above) was prepared equal to the number of samples plus one to insure there is enough for all tubes. Add 49 µL of the Master Mix to each tube. Add 1 µL of sample to each tube (Perkin Elmer, Part No. N801-0933). The tubes were centrifuged 600 rpm for 3 minutes and transfered to thermocycler (Perkin Elmer, ABI Prism 7700 Sequence Detector). The thermocycler was programmed to use the following conditions in sequence:

50° C. for 2 minutes.
95° C. for 10 minutes.
Denaturation step 94° C. for 15 seconds.
Annealing step 60° C. for 1 minute.

Repeat steps 3.1.6.4 to 3.1.6.5 for an additional 39 cycles. The total number of cycles is 40.

Hold step (4° C. on hold).

Example 7

Evaluation of In Vivo CTL Response

C57BU6 mice (2 mice per dose) were injected intravenously with $9 \times 10^9$ particles/animal (iv/200 µl) of a recombinant adenoviral vector encoding the βgal reporter gene under control of the CMV promoter. Naive mice were employed as controls. The spleens were harvested at day 10 for immunological analysis. Livers were harvested for analysis of β-gal transgene expression. Cells were be dispersed to a single cell suspension and washed 3 times. The cells were be resuspended complete RPMI-10 (RPMI+10% FCS, 2ME (5 µM), glutamine, Na pyruvate, Pen/Strep). Responder CTL cells were seeded in 24-well plates at $8 \times 10^6$ cells per well in 1.5 ml RPMI-5%. The responder CTL cells were restimulated by adding syngeneic (C57BL/6) spleen cells that were transduced for 6 hours with $2 \times 10^{10}$ BGCG particles/ml and then mitomycin treated to inhibit proliferation and/or activation of stimulator cell populations. The responder CTL were co-cultured with the stimulator cells at 37° C. in a humidified incubator for seven days. Concanavilin A supernate (10%) was added to the CTL restimulation cultures on day 2 to promote CTL expansion. The Effector CTL cells were harvested, washed 2 times and counted to enumerate the CTL effector cells. The CTL blast cells were plated in 96-well plates (round-bottom) at various cell densities with $1 \times 10^4$ $^{51}$Cr-labeled P815 target cells expressing antigen (EL4 target cells were transduced overnight with $1 \times 10^{10}$ PN/ml BGCG to induce antigen expression and then labeled 2 hr with 51-chromium) to give various Effector to target ratios in a total volume of 200 µl RPMI-10. The Effector CTL cells were co-cultivated with the target cells for 6 hours and the specific $^{51}$Cr release were determined by counting harvested supernates (100 µl) in the γ counter.

Example 8

Gel Shift Assays for Nf-kB and AP-1

Double-stranded oligonucleotides containing high-affinity binding sites for NF-kB (Promega E329) or AP-1 (Promega E320) were labeled using [g-32P]ATP (3,000 Ci/mmol) and T4 polynucleotide kinase and purified using MicroSpin G-25 columns. Nuclear extracts (1 µg protein) were incubated in a 10 µl (final volume) reaction mixture containing 10 mM Tris-HCl (pH 7.5), 0.5 mM DTT, 0.5 mM EDTA, 1 mM MgCl2, 4% glycerol and 50 ng/ml poly(dI-dC) at room temperature for 10 min. Labeled oligonucleotides (~100,000 cpm) were then added and the reaction mixtures were incubated for another 20 min at room temperature. After 20 min incubation, 5 µl of 60% glycerol was added to each reaction and the samples were subjected to native polyacrylamide gel electrophoresis. After electrophoresis gels were dried and exposed to an X-ray film at −70° C.

We claim:

1. A method of increasing the infectivity of a cell to a viral vector by treatment of the cell with a micro-calpain inhibitor wherein said method is practiced ex vivo, and wherein said method comprises selecting a cell whose infectivity is to be increased, and co-administering said micro-calpain inhibitor and said viral vector to said cell.

2. The method of claim 1 wherein said viral vector is an adenoviral Vector.

3. The method of claim 2 wherein the micro-calpain inhibitor is calpain inhibitor 1.

4. The method of claim 2 wherein said adenoviral vector is replication deficient.

5. The method of claim 4 wherein said replication deficient adenoviral vector comprises a therapeutic transgene.

6. The method of claim 1 where said transgene is selected from the group consisting of cytostatic genes and pro-apoptotic genes.

7. The method of claim 6 wherein the gene is a cytostatic gene.

8. The method of claim 7 wherein the gene is the p21 gene.

9. The method of claim 6 wherein the gene is a pro-apoptotic gene.

10. The method of claim 9 wherein the gene is p53.

11. The method of claim 1 wherein the vector is replication competent.

12. The method of claim 11 wherein the replication competent vector is a conditionally replicating viral vector.

13. The method of claim 12 wherein the conditionally replicating viral vector further comprises an expression cassette which expresses a pro-apoptotic gene.

14. The method of claim 13 wherein the pro-apoptotic gene is the E3-11.6K gene.

15. The method of claim 14 wherein the viral vector is a replication deficient adenoviral vector and the cell is a producer cell capable of complementing the deleted functions of the replication deficient adenoviral vector.

16. The method of claim 15 wherein the replication deficient adenoviral vector lacks a functional E1 region and the producer cell is a 293 cell.

17. The method of claim 1 wherein said method is practiced in a process to purge tumor cells from a stem cell product by exposing said stem cell product to a micro-calpain inhibitor prior to the administration of a viral vector.

18. The method of claim 17 wherein said viral vector is an adenoviral vector that encodes and expresses the p53 tumor suppressor gene.

19. A method of infecting a human cell with a virus, comprising:

contacting said cell ex vivo with an amount of a micro-calpain inhibitor sufficient to increase the infectivity of said cell to said virus; and co-administering said virus to said cell.

* * * * *

UNITED STATES PATENT AND TRADEMARK OFFICE
CERTIFICATE OF CORRECTION

| | | |
|---|---|---|
| PATENT NO. | : 7,001,770 B1 | Page 1 of 1 |
| APPLICATION NO. | : 09/416735 | |
| DATED | : February 21, 2006 | |
| INVENTOR(S) | : Atencio et al. | |

It is certified that error appears in the above-identified patent and that said Letters Patent is hereby corrected as shown below:

Column 35,
Line 26, replace "1" with -- 5 --.

Signed and Sealed this

Twentieth Day of June, 2006

JON W. DUDAS
*Director of the United States Patent and Trademark Office*